United States Patent
Malecki et al.

(10) Patent No.: US 9,085,464 B2
(45) Date of Patent: Jul. 21, 2015

(54) RESISTANCE MEASUREMENT SYSTEM AND METHOD OF USING THE SAME

(75) Inventors: Harry C. Malecki, Abingdon, MD (US); Randy L. Gaigler, Parkville, MD (US); Corey A. Fleischer, Timonium, MD (US); Han Liu, Lutherville-Timonium, MD (US); Brandon K. Malet, Baltimore, MD (US); Samuel J. Markkula, Rising Sun, MD (US)

(73) Assignee: APPLIED NANOSTRUCTURED SOLUTIONS, LLC, Baltimore, MD (US)

( * ) Notice: Subject to any disclaimer, the term of this patent is extended or adjusted under 35 U.S.C. 154(b) by 37 days.

(21) Appl. No.: 13/414,669

(22) Filed: Mar. 7, 2012

(65) Prior Publication Data

US 2013/0236631 A1    Sep. 12, 2013

(51) Int. Cl.
| | |
|---|---|
| C23C 16/00 | (2006.01) |
| C01B 31/02 | (2006.01) |
| B82Y 30/00 | (2011.01) |
| B82Y 40/00 | (2011.01) |
| C23C 16/52 | (2006.01) |
| G01R 27/08 | (2006.01) |
| D04H 1/00 | (2006.01) |
| D04H 3/00 | (2012.01) |
| D04H 5/00 | (2012.01) |
| D04H 13/00 | (2006.01) |
| B32B 17/12 | (2006.01) |
| B32B 18/00 | (2006.01) |
| B32B 27/04 | (2006.01) |
| B32B 27/12 | (2006.01) |
| G01N 27/04 | (2006.01) |
| B82Y 35/00 | (2011.01) |

(52) U.S. Cl.
CPC ............. *C01B 31/0206* (2013.01); *B82Y 30/00* (2013.01); *B82Y 40/00* (2013.01); *B82Y 35/00* (2013.01); *G01N 27/04* (2013.01)

(58) Field of Classification Search
CPC ........ B82Y 30/00; B82Y 40/00; B82Y 35/00; C01B 31/0206; G01N 27/04
USPC ........................ 427/248.1, 249.1, 8; 324/693; 428/292.1, 293.4, 297.4
See application file for complete search history.

(56) References Cited

U.S. PATENT DOCUMENTS

| | | | |
|---|---|---|---|
| 2,883,306 | A | 4/1959 | Cotter |
| 2,883,396 | A | 4/1959 | Cotter |

(Continued)

FOREIGN PATENT DOCUMENTS

| | | |
|---|---|---|
| CN | 1363123 A | 8/2002 |
| CN | 1838999 A | 9/2006 |

(Continued)

OTHER PUBLICATIONS

Parikh et al. Flexible vapour sensors using single walled carbon nanotubes, Sensors and Actuators B, 113, 2006 pp. 55-63.*

(Continued)

*Primary Examiner* — Kelly M Gambetta
(74) *Attorney, Agent, or Firm* — McDermott Will & Emery LLP

(57) ABSTRACT

A quality control system for the manufacture of carbon nanostructure-laden substrates includes a resistance measurement module for continuously measuring resistance of the carbon nanostructure (CNS)-laden substrate.

20 Claims, 6 Drawing Sheets

(56) References Cited

U.S. PATENT DOCUMENTS

| | | | |
|---|---|---|---|
| 3,580,731 A | 5/1971 | Milewski et al. |
| 4,065,592 A | 12/1977 | McAllister |
| 4,104,083 A | 8/1978 | Hirano |
| 4,313,084 A | 1/1982 | Hosokawa et al. |
| 4,488,203 A | 12/1984 | Muranaka et al. |
| 4,515,107 A | 5/1985 | Fournier et al. |
| 4,530,750 A | 7/1985 | Alsenberg et al. |
| 4,581,284 A | 4/1986 | Eggert et al. |
| 4,707,349 A | 11/1987 | Hjersted |
| 4,920,917 A | 5/1990 | Nakatani et al. |
| 5,093,155 A | 3/1992 | Miyazaki et al. |
| 5,103,067 A | 4/1992 | Aldissi |
| 5,130,194 A | 7/1992 | Baker et al. |
| 5,156,225 A | 10/1992 | Murrin |
| 5,173,367 A | 12/1992 | Liimatta et al. |
| 5,175,224 A | 12/1992 | Horacek |
| 5,187,021 A | 2/1993 | Vydra et al. |
| 5,221,605 A | 6/1993 | Bard et al. |
| 5,238,808 A | 8/1993 | Bard et al. |
| 5,246,794 A | 9/1993 | Blomgren et al. |
| 5,310,687 A | 5/1994 | Bard et al. |
| 5,449,574 A | 9/1995 | Higley |
| 5,470,408 A | 11/1995 | Nielson et al. |
| 5,514,217 A | 5/1996 | Niino et al. |
| 5,547,525 A | 8/1996 | Bennett et al. |
| 5,571,749 A | 11/1996 | Matsuda et al. |
| 5,581,438 A | 12/1996 | Halliop |
| 5,583,318 A | 12/1996 | Powell |
| 5,639,984 A | 6/1997 | Nielson |
| 5,707,758 A | 1/1998 | Iwatsu et al. |
| 5,714,089 A | 2/1998 | Bard et al. |
| 5,731,147 A | 3/1998 | Bard et al. |
| 5,891,306 A * | 4/1999 | Chase et al. ............... 162/198 |
| 5,908,585 A | 6/1999 | Shibuta |
| 5,949,018 A | 9/1999 | Esker |
| 5,968,274 A | 10/1999 | Fujioka et al. |
| 5,997,832 A | 12/1999 | Lieber et al. |
| 6,139,956 A | 10/2000 | Endoh et al. |
| 6,140,138 A | 10/2000 | Bard et al. |
| 6,146,783 A | 11/2000 | Brohm et al. |
| 6,180,281 B1 | 1/2001 | Schneider et al. |
| 6,184,280 B1 | 2/2001 | Shibuta |
| 6,194,685 B1 | 2/2001 | Rutherford |
| 6,221,154 B1 | 4/2001 | Lee et al. |
| 6,225,565 B1 | 5/2001 | Prysner |
| 6,232,706 B1 | 5/2001 | Dai et al. |
| 6,233,135 B1 | 5/2001 | Farahmandi et al. |
| 6,251,520 B1 | 6/2001 | Blizzard et al. |
| 6,265,466 B1 | 7/2001 | Glatkowski et al. |
| 6,331,209 B1 | 12/2001 | Jang et al. |
| 6,333,016 B1 | 12/2001 | Resasco et al. |
| 6,361,861 B2 | 3/2002 | Gao |
| 6,413,487 B1 | 7/2002 | Resasco et al. |
| 6,420,293 B1 | 7/2002 | Chang et al. |
| 6,430,031 B1 | 8/2002 | Dispennette et al. |
| 6,454,816 B1 | 9/2002 | Lee et al. |
| 6,455,021 B1 | 9/2002 | Saito |
| 6,465,057 B1 | 10/2002 | Nakahigashi et al. |
| 6,479,028 B1 | 11/2002 | Kaner et al. |
| 6,479,030 B1 | 11/2002 | Firsich |
| 6,491,789 B2 | 12/2002 | Niu |
| 6,495,258 B1 | 12/2002 | Chen et al. |
| 6,528,572 B1 | 3/2003 | Patel et al. |
| 6,564,744 B2 | 5/2003 | Nakahigashi et al. |
| 6,585,152 B2 | 7/2003 | Farahmandi et al. |
| 6,602,742 B2 | 8/2003 | Maletin et al. |
| 6,639,786 B2 | 10/2003 | Noguchi et al. |
| 6,650,531 B2 | 11/2003 | Ikeda et al. |
| 6,653,619 B2 | 11/2003 | Chin et al. |
| 6,673,392 B2 | 1/2004 | Lee et al. |
| 6,686,537 B1 | 2/2004 | Gareis et al. |
| 6,692,717 B1 | 2/2004 | Smalley et al. |
| 6,765,949 B2 | 7/2004 | Chang |
| 6,773,466 B1 | 8/2004 | Hiratsuka et al. |
| 6,790,425 B1 | 9/2004 | Smalley et al. |
| 6,818,821 B2 | 11/2004 | Fujieda et al. |
| 6,831,826 B2 | 12/2004 | Iwaida et al. |
| 6,837,928 B1 | 1/2005 | Zhang et al. |
| 6,852,410 B2 | 2/2005 | Veedu et al. |
| 6,863,942 B2 | 3/2005 | Ren et al. |
| 6,887,365 B2 | 5/2005 | Naughton |
| 6,887,451 B2 | 5/2005 | Dodelet et al. |
| 6,900,264 B2 | 5/2005 | Kumar et al. |
| 6,900,580 B2 | 5/2005 | Dai et al. |
| 6,908,572 B1 | 6/2005 | Derbyshire et al. |
| 6,913,075 B1 | 7/2005 | Knowles et al. |
| 6,934,600 B2 | 8/2005 | Jang et al. |
| 6,936,653 B2 | 8/2005 | McElrath et al. |
| 6,949,237 B2 | 9/2005 | Smalley et al. |
| 6,955,800 B2 | 10/2005 | Resasco et al. |
| 6,962,892 B2 | 11/2005 | Resasco et al. |
| 6,967,013 B2 | 11/2005 | Someya et al. |
| 6,979,709 B2 | 12/2005 | Smalley et al. |
| 6,986,853 B2 | 1/2006 | Glatkowski et al. |
| 6,986,877 B2 | 1/2006 | Takikawa et al. |
| 6,994,907 B2 | 2/2006 | Resasco et al. |
| 7,011,760 B2 | 3/2006 | Wang et al. |
| 7,018,600 B2 | 3/2006 | Yanagisawa et al. |
| 7,022,776 B2 | 4/2006 | Bastiaens et al. |
| 7,045,108 B2 | 5/2006 | Jiang et al. |
| 7,056,452 B2 | 6/2006 | Niu et al. |
| 7,060,326 B2 | 6/2006 | Hiel et al. |
| 7,061,749 B2 | 6/2006 | Liu et al. |
| 7,074,294 B2 | 7/2006 | Dubrow |
| 7,085,125 B2 | 8/2006 | Sung |
| 7,094,386 B2 | 8/2006 | Resasco et al. |
| 7,105,596 B2 | 9/2006 | Smalley et al. |
| 7,108,841 B2 | 9/2006 | Smalley et al. |
| 7,118,693 B2 | 10/2006 | Glatkowski et al. |
| 7,125,502 B2 | 10/2006 | Smalley et al. |
| 7,125,534 B1 | 10/2006 | Smalley et al. |
| 7,132,621 B2 | 11/2006 | Kumar et al. |
| 7,144,563 B2 | 12/2006 | Rao et al. |
| 7,147,966 B2 | 12/2006 | Ren et al. |
| 7,148,619 B2 | 12/2006 | Ken et al. |
| 7,151,129 B2 | 12/2006 | Ishikawa et al. |
| 7,153,452 B2 | 12/2006 | Ogale et al. |
| 7,157,068 B2 | 1/2007 | Li et al. |
| 7,160,532 B2 | 1/2007 | Liu et al. |
| 7,189,959 B1 | 3/2007 | Morison et al. |
| 7,211,320 B1 | 5/2007 | Cooper et al. |
| 7,226,643 B2 | 6/2007 | Juang et al. |
| 7,235,159 B2 | 6/2007 | Gu et al. |
| 7,253,442 B2 | 8/2007 | Huang et al. |
| 7,261,779 B2 | 8/2007 | Gardner |
| 7,265,174 B2 | 9/2007 | Carroll et al. |
| 7,265,175 B2 | 9/2007 | Winey et al. |
| 7,278,324 B2 | 10/2007 | Smits et al. |
| 7,282,260 B2 | 10/2007 | LeGrande |
| 7,289,312 B2 | 10/2007 | Duff, Jr. |
| 7,294,302 B2 | 11/2007 | Kolde et al. |
| 7,312,608 B2 | 12/2007 | Georgeson et al. |
| 7,329,698 B2 | 2/2008 | Noguchi et al. |
| 7,338,684 B1 | 3/2008 | Curliss et al. |
| 7,340,134 B1 | 3/2008 | Hudson, II et al. |
| 7,352,559 B2 | 4/2008 | Sung |
| 7,354,877 B2 | 4/2008 | Rosenberger et al. |
| 7,354,881 B2 | 4/2008 | Resasco et al. |
| 7,354,988 B2 | 4/2008 | Charati et al. |
| 7,372,880 B2 | 5/2008 | Jablonski et al. |
| 7,384,663 B2 | 6/2008 | Olry et al. |
| 7,399,794 B2 | 7/2008 | Harmon et al. |
| 7,407,640 B2 | 8/2008 | Barrera et al. |
| 7,407,901 B2 | 8/2008 | Bystricky et al. |
| 7,410,628 B2 | 8/2008 | Bening et al. |
| 7,419,601 B2 | 9/2008 | Cooper et al. |
| 7,431,965 B2 | 10/2008 | Grigorian et al. |
| 7,435,476 B2 | 10/2008 | Viswanathan et al. |
| 7,442,284 B2 | 10/2008 | Ren et al. |
| 7,445,817 B2 | 11/2008 | Kumar et al. |
| 7,448,441 B2 | 11/2008 | Hendricks et al. |
| 7,448,931 B2 | 11/2008 | Liu et al. |
| 7,449,631 B2 | 11/2008 | Lee et al. |
| 7,459,627 B2 | 12/2008 | Lee et al. |

(56) References Cited

U.S. PATENT DOCUMENTS

| | | | |
|---|---|---|---|
| 7,465,605 B2 | 12/2008 | Raravikar et al. |
| 7,466,539 B2 | 12/2008 | Dementiev et al. |
| 7,473,466 B1 | 1/2009 | Muradov |
| 7,479,052 B2 | 1/2009 | Kim et al. |
| 7,488,455 B2 | 2/2009 | Dai et al. |
| 7,504,078 B1 | 3/2009 | Jacques et al. |
| 7,510,695 B2 | 3/2009 | Smalley et al. |
| 7,610,695 B2 | 3/2009 | Smalley et al. |
| 7,531,267 B2 | 5/2009 | Kim |
| 7,532,454 B2 | 5/2009 | Plee et al. |
| 7,534,486 B2 | 5/2009 | Boerstoel et al. |
| 7,553,341 B2 | 6/2009 | Pan et al. |
| 7,563,411 B2 | 7/2009 | Jiang et al. |
| 7,563,428 B2 | 7/2009 | Resasco et al. |
| 7,569,425 B2 | 8/2009 | Huang et al. |
| 7,579,112 B2 | 8/2009 | Chiang et al. |
| 7,588,700 B2 | 9/2009 | Kwon et al. |
| 7,592,248 B2 | 9/2009 | Ventzek et al. |
| 7,597,869 B2 | 10/2009 | Hsiao |
| 7,608,798 B2 | 10/2009 | Kumar et al. |
| 7,611,579 B2 | 11/2009 | Lashmore et al. |
| 7,612,985 B2 | 11/2009 | Dementiev et al. |
| 7,615,204 B2 | 11/2009 | Ajayan et al. |
| 7,615,205 B2 | 11/2009 | Jiang et al. |
| 7,632,550 B2 | 12/2009 | Mizuno et al. |
| 7,632,569 B2 | 12/2009 | Smalley et al. |
| 7,700,943 B2 | 4/2010 | Raravikar et al. |
| 7,709,087 B2 | 5/2010 | Majidi et al. |
| 7,718,220 B2 | 5/2010 | D'Silva et al. |
| 7,771,798 B1 | 8/2010 | Grosse et al. |
| 7,776,777 B2 | 8/2010 | Kim et al. |
| 7,793,653 B2 | 9/2010 | Kuckelkorn et al. |
| 7,811,632 B2 | 10/2010 | Eres |
| 7,815,820 B2 | 10/2010 | Tan et al. |
| 7,816,709 B2 | 10/2010 | Balzano et al. |
| 7,820,329 B2 | 10/2010 | Boulton et al. |
| 7,862,795 B2 | 1/2011 | Zhang et al. |
| 7,871,591 B2 | 1/2011 | Harutyunyan et al. |
| 7,880,376 B2 | 2/2011 | Takai et al. |
| 7,927,701 B2 | 4/2011 | Curliss et al. |
| 8,373,971 B2 | 2/2013 | Young |
| 2002/0035170 A1 | 3/2002 | Glatkowski et al. |
| 2002/0048143 A1 | 4/2002 | Lee et al. |
| 2002/0085968 A1 | 7/2002 | Smalley et al. |
| 2002/0090330 A1 | 7/2002 | Smalley et al. |
| 2002/0098135 A1 | 7/2002 | Smalley et al. |
| 2002/0136683 A1 | 9/2002 | Smalley et al. |
| 2003/0042147 A1 | 3/2003 | Talin et al. |
| 2003/0044678 A1 | 3/2003 | ESq. |
| 2003/0055153 A1 | 3/2003 | Luippold et al. |
| 2003/0102585 A1 | 6/2003 | Poulin et al. |
| 2003/0111333 A1 | 6/2003 | Montgomery et al. |
| 2003/0143453 A1 | 7/2003 | Ren et al. |
| 2004/0007955 A1 | 1/2004 | Yaniv et al. |
| 2004/0018375 A1 | 1/2004 | Banno et al. |
| 2004/0020681 A1 | 2/2004 | Hjortstam et al. |
| 2004/0026234 A1 | 2/2004 | Vanden Brande et al. |
| 2004/0029019 A1 | 2/2004 | Clarke et al. |
| 2004/0055631 A1 | 3/2004 | Szymocha et al. |
| 2004/0071870 A1 | 4/2004 | Knowles et al. |
| 2004/0082247 A1 | 4/2004 | Desai et al. |
| 2004/0096389 A1 | 5/2004 | Lobovsky et al. |
| 2004/0105807 A1 | 6/2004 | Fan et al. |
| 2004/0111141 A1 | 6/2004 | Brabec et al. |
| 2004/0166417 A1 | 8/2004 | Nishio et al. |
| 2004/0184981 A1 | 9/2004 | Liu et al. |
| 2004/0197546 A1 | 10/2004 | Rinzler et al. |
| 2004/0210289 A1 | 10/2004 | Wang et al. |
| 2004/0241532 A1 | 12/2004 | Kim |
| 2004/0245088 A1 | 12/2004 | Gardner |
| 2004/0253167 A1 | 12/2004 | Silva et al. |
| 2005/0090176 A1 | 4/2005 | Dean et al. |
| 2005/0100501 A1 | 5/2005 | Veedu et al. |
| 2005/0112052 A1 | 5/2005 | Gu et al. |
| 2005/0113876 A1 | 5/2005 | Weiner et al. |
| 2005/0119371 A1 | 6/2005 | Drzal et al. |
| 2005/0150620 A1* | 7/2005 | Hamada et al. ............... 162/152 |
| 2005/0170177 A1 | 8/2005 | Crawford et al. |
| 2005/0172370 A1 | 8/2005 | Haq et al. |
| 2005/0176329 A1 | 8/2005 | Olry et al. |
| 2005/0188727 A1 | 9/2005 | Greywall |
| 2005/0214648 A1 | 9/2005 | Boulton et al. |
| 2005/0231893 A1 | 10/2005 | Harvey |
| 2005/0238810 A1 | 10/2005 | Scaringe et al. |
| 2005/0260412 A1 | 11/2005 | Gardner |
| 2005/0263456 A1 | 12/2005 | Cooper et al. |
| 2005/0287064 A1 | 12/2005 | Mayne et al. |
| 2006/0052509 A1 | 3/2006 | Saitoh |
| 2006/0054866 A1 | 3/2006 | Ait-Haddou et al. |
| 2006/0063065 A1 | 3/2006 | Clarke et al. |
| 2006/0110599 A1 | 5/2006 | Honma et al. |
| 2006/0121275 A1 | 6/2006 | Poulin et al. |
| 2006/0126268 A1 | 6/2006 | Sung |
| 2006/0159916 A1 | 7/2006 | Dubrow et al. |
| 2006/0177602 A1 | 8/2006 | Dijon et al. |
| 2006/0198956 A1 | 9/2006 | Eres |
| 2006/0233692 A1 | 10/2006 | Scaringe et al. |
| 2006/0241236 A1 | 10/2006 | Kuznetsov et al. |
| 2006/0249203 A1 | 11/2006 | Li et al. |
| 2006/0253942 A1 | 11/2006 | Barrera et al. |
| 2007/0020167 A1 | 1/2007 | Han et al. |
| 2007/0036709 A1 | 2/2007 | Lashmore et al. |
| 2007/0048521 A1 | 3/2007 | Istvan |
| 2007/0054105 A1 | 3/2007 | Hsiao |
| 2007/0062799 A1 | 3/2007 | Lee |
| 2007/0070579 A1 | 3/2007 | Sung |
| 2007/0076349 A1 | 4/2007 | Dementiev et al. |
| 2007/0092431 A1 | 4/2007 | Resasco et al. |
| 2007/0110977 A1 | 5/2007 | Al-Haik et al. |
| 2007/0128960 A1 | 6/2007 | Ghasemi Nejhad et al. |
| 2007/0134555 A1 | 6/2007 | Ren et al. |
| 2007/0135588 A1 | 6/2007 | Diakoumakos et al. |
| 2007/0166603 A1 | 7/2007 | Nakanishi et al. |
| 2007/0189953 A1 | 8/2007 | Bai et al. |
| 2007/0237990 A1 | 10/2007 | Kim |
| 2007/0241962 A1 | 10/2007 | Shinoda et al. |
| 2007/0259128 A1 | 11/2007 | Parsapour |
| 2007/0293086 A1 | 12/2007 | Liu et al. |
| 2008/0010796 A1 | 1/2008 | Pan et al. |
| 2008/0014431 A1 | 1/2008 | Lashmore et al. |
| 2008/0020193 A1 | 1/2008 | Jang et al. |
| 2008/0048364 A1 | 2/2008 | Armeniades et al. |
| 2008/0049380 A1 | 2/2008 | Miyahara et al. |
| 2008/0053922 A1 | 3/2008 | Honsinger, Jr. et al. |
| 2008/0057265 A1 | 3/2008 | Liang et al. |
| 2008/0063585 A1* | 3/2008 | Smalley et al. ............... 423/414 |
| 2008/0075954 A1 | 3/2008 | Wardle et al. |
| 2008/0102371 A1 | 5/2008 | Mitchell et al. |
| 2008/0117562 A1 | 5/2008 | Maruyama et al. |
| 2008/0118753 A1 | 5/2008 | Poulin et al. |
| 2008/0137890 A1 | 6/2008 | Petersen et al. |
| 2008/0146440 A1 | 6/2008 | Westin et al. |
| 2008/0160286 A1 | 7/2008 | Asrar et al. |
| 2008/0170982 A1 | 7/2008 | Zhang et al. |
| 2008/0173111 A1 | 7/2008 | Thostenson et al. |
| 2008/0182108 A1 | 7/2008 | Curliss et al. |
| 2008/0187482 A1 | 8/2008 | Chen et al. |
| 2008/0187648 A1 | 8/2008 | Hart et al. |
| 2008/0195187 A1 | 8/2008 | Li et al. |
| 2008/0212261 A1 | 9/2008 | Ajayan et al. |
| 2008/0247938 A1 | 10/2008 | Tsai et al. |
| 2008/0248192 A1 | 10/2008 | Long et al. |
| 2008/0248362 A1 | 10/2008 | Sayre et al. |
| 2008/0251971 A1 | 10/2008 | Kim et al. |
| 2008/0254675 A1 | 10/2008 | Lee et al. |
| 2008/0273290 A1 | 11/2008 | Dementiev et al. |
| 2008/0279753 A1 | 11/2008 | Harutyunyan |
| 2008/0286564 A1 | 11/2008 | Tsotsis |
| 2008/0296558 A1 | 12/2008 | Choi et al. |
| 2008/0297980 A1 | 12/2008 | Bourcier et al. |
| 2008/0299308 A1 | 12/2008 | Luo et al. |
| 2009/0017301 A1 | 1/2009 | Moireau |
| 2009/0020734 A1 | 1/2009 | Jang et al. |
| 2009/0029127 A1 | 1/2009 | Watanabe et al. |

(56) References Cited

U.S. PATENT DOCUMENTS

| | | |
|---|---|---|
| 2009/0047453 A1 | 2/2009 | Folaron et al. |
| 2009/0047502 A1 | 2/2009 | Folaron et al. |
| 2009/0053512 A1 | 2/2009 | Pyun et al. |
| 2009/0059474 A1 | 3/2009 | Zhamu et al. |
| 2009/0068387 A1 | 3/2009 | Panzer et al. |
| 2009/0068461 A1 | 3/2009 | Reneker et al. |
| 2009/0072222 A1 | 3/2009 | Radisic et al. |
| 2009/0081383 A1 | 3/2009 | Alberding et al. |
| 2009/0081441 A1 | 3/2009 | Shah et al. |
| 2009/0087743 A1 | 4/2009 | Kim et al. |
| 2009/0092832 A1 | 4/2009 | Moireau |
| 2009/0095051 A1 | 4/2009 | Suzuki et al. |
| 2009/0098453 A1 | 4/2009 | Liu et al. |
| 2009/0099016 A1 | 4/2009 | Carruthers et al. |
| 2009/0117269 A1 | 5/2009 | Hansen et al. |
| 2009/0121219 A1 | 5/2009 | Song et al. |
| 2009/0126783 A1 | 5/2009 | Lin et al. |
| 2009/0136707 A1 | 5/2009 | Ueno |
| 2009/0140098 A1 | 6/2009 | Lengsfeld et al. |
| 2009/0176100 A1 | 7/2009 | Higashi et al. |
| 2009/0176112 A1 | 7/2009 | Kruckenberg et al. |
| 2009/0181309 A1 | 7/2009 | Kwon et al. |
| 2009/0185327 A1 | 7/2009 | Seymour |
| 2009/0186214 A1 | 7/2009 | Lafdi et al. |
| 2009/0186276 A1 | 7/2009 | Zhamu et al. |
| 2009/0191352 A1 | 7/2009 | DuFaux et al. |
| 2009/0192241 A1 | 7/2009 | Raravikar et al. |
| 2009/0194313 A1 | 8/2009 | Jiang et al. |
| 2009/0208743 A1 | 8/2009 | Pettit |
| 2009/0212430 A1 | 8/2009 | Wyland |
| 2009/0214800 A1 | 8/2009 | Saito |
| 2009/0214944 A1 | 8/2009 | Rojeski |
| 2009/0220409 A1 | 9/2009 | Curliss et al. |
| 2009/0226673 A1 | 9/2009 | Friedersdorf et al. |
| 2009/0244810 A1 | 10/2009 | Reynolds |
| 2009/0255706 A1 | 10/2009 | Jiang et al. |
| 2009/0258164 A1 | 10/2009 | Nakai et al. |
| 2009/0262484 A1 | 10/2009 | Miyagi |
| 2009/0272946 A1 | 11/2009 | Lu |
| 2009/0282671 A1 | 11/2009 | Tao et al. |
| 2009/0286079 A1 | 11/2009 | Barker et al. |
| 2009/0294022 A1 | 12/2009 | Hayes et al. |
| 2009/0294753 A1 | 12/2009 | Hauge et al. |
| 2009/0305135 A1 | 12/2009 | Shi et al. |
| 2009/0311166 A1 | 12/2009 | Hart et al. |
| 2009/0314510 A1 | 12/2009 | Kukowski et al. |
| 2009/0325076 A1 | 12/2009 | Matsui et al. |
| 2010/0000520 A1 | 1/2010 | Vachon |
| 2010/0000754 A1 | 1/2010 | Mann et al. |
| 2010/0000770 A1 | 1/2010 | Gupta et al. |
| 2010/0035124 A1 | 2/2010 | Thompson et al. |
| 2010/0059243 A1 | 3/2010 | Chang |
| 2010/0074834 A1 | 3/2010 | Kim |
| 2010/0087042 A1 | 4/2010 | Kim et al. |
| 2010/0098931 A1 | 4/2010 | Daniel et al. |
| 2010/0099319 A1 | 4/2010 | Lashmore et al. |
| 2010/0159240 A1 | 6/2010 | Shah et al. |
| 2010/0173228 A1 | 7/2010 | Wallace et al. |
| 2010/0178531 A1 | 7/2010 | Amaratunga et al. |
| 2010/0178825 A1 | 7/2010 | Shah et al. |
| 2010/0188833 A1 | 7/2010 | Liang et al. |
| 2010/0192851 A1 | 8/2010 | Shah et al. |
| 2010/0196695 A1 | 8/2010 | Garcia et al. |
| 2010/0196697 A1 | 8/2010 | D'Silva et al. |
| 2010/0197848 A1 | 8/2010 | Verghese et al. |
| 2010/0203362 A1 | 8/2010 | Lam et al. |
| 2010/0206504 A1 | 8/2010 | Akiyama et al. |
| 2010/0210159 A1 | 8/2010 | Zhu |
| 2010/0221424 A1 | 9/2010 | Malecki et al. |
| 2010/0224129 A1 | 9/2010 | Malecki et al. |
| 2010/0227134 A1 | 9/2010 | Shah et al. |
| 2010/0227155 A1 | 9/2010 | Bao et al. |
| 2010/0254885 A1 | 10/2010 | Menchhofer et al. |
| 2010/0258111 A1 | 10/2010 | Shah et al. |
| 2010/0270069 A1 | 10/2010 | Shar et al. |
| 2010/0270513 A1 | 10/2010 | Haylock et al. |
| 2010/0271253 A1 | 10/2010 | Shah et al. |
| 2010/0272891 A1 | 10/2010 | Malecki et al. |
| 2010/0276072 A1 | 11/2010 | Shah et al. |
| 2010/0279569 A1 | 11/2010 | Shah et al. |
| 2010/0286395 A1 | 11/2010 | Newkome et al. |
| 2010/0311866 A1 | 12/2010 | Huang et al. |
| 2010/0330421 A1 | 12/2010 | Cui et al. |
| 2011/0024409 A1 | 2/2011 | Shah et al. |
| 2011/0024694 A1 | 2/2011 | Shah et al. |
| 2011/0036829 A1 | 2/2011 | Fugetsu et al. |
| 2011/0089958 A1* | 4/2011 | Malecki et al. ............... 324/693 |
| 2011/0104571 A1 | 5/2011 | Zhamu et al. |
| 2011/0123735 A1 | 5/2011 | Shah et al. |
| 2011/0124253 A1 | 5/2011 | Shah et al. |
| 2011/0124483 A1 | 5/2011 | Shah et al. |
| 2011/0143087 A1 | 6/2011 | Alberding et al. |
| 2011/0159365 A1 | 6/2011 | Loveness et al. |
| 2011/0159381 A1 | 6/2011 | Doe et al. |
| 2011/0163274 A1 | 7/2011 | Plee et al. |
| 2011/0171469 A1 | 7/2011 | Shah et al. |
| 2011/0174519 A1 | 7/2011 | Shah et al. |
| 2011/0186775 A1 | 8/2011 | Shah et al. |
| 2011/0216476 A1 | 9/2011 | Fleischer et al. |
| 2011/0235240 A1 | 9/2011 | Lu et al. |
| 2011/0242731 A1 | 10/2011 | Fleischer et al. |
| 2011/0281068 A1 | 11/2011 | David et al. |
| 2011/0287318 A1 | 11/2011 | Loveness et al. |
| 2011/0297892 A1 | 12/2011 | Shah et al. |
| 2011/0304964 A1 | 12/2011 | Fleischer et al. |
| 2012/0000691 A1 | 1/2012 | Shah et al. |
| 2012/0052363 A1 | 3/2012 | Fleischer et al. |

FOREIGN PATENT DOCUMENTS

| | | |
|---|---|---|
| CN | 1970612 A | 5/2007 |
| CN | 101189930 A | 5/2008 |
| CN | 101365740 A | 2/2009 |
| CN | 101654555 A | 2/2010 |
| CN | 101698975 | 4/2010 |
| IN | 01900DE2008 A | 3/2010 |
| JP | 61-157495 | 7/1986 |
| JP | H-05-269874 A | 10/1993 |
| JP | H 07-134911 | 5/1995 |
| JP | H 11-134949 | 5/1999 |
| JP | 2001-517583 A | 10/2001 |
| JP | 2002-515847 A | 5/2002 |
| JP | 2003-239171 A | 8/2003 |
| JP | 2004-039668 | 2/2004 |
| JP | 2004/247064 A | 9/2004 |
| JP | 2005-353493 | 12/2005 |
| JP | 2005-538026 | 12/2005 |
| JP | 2007-070593 A | 3/2007 |
| JP | 2007-515364 | 6/2007 |
| JP | 2007-194354 A | 8/2007 |
| JP | 2007-220841 | 8/2007 |
| JP | 2007-246317 A | 9/2007 |
| JP | 2008-010329 | 1/2008 |
| JP | 2008-270807 | 11/2008 |
| JP | 2008-296338 A | 12/2008 |
| JP | 2009-173476 | 8/2009 |
| JP | 2009-190948 | 8/2009 |
| JP | 2009-533831 | 9/2009 |
| JP | 2009-252745 | 10/2009 |
| JP | 2009-535530 A | 10/2009 |
| JP | 2009-537339 | 10/2009 |
| KR | 100829001 | 5/2008 |
| TW | 200833861 | 8/2008 |
| WO | WO 03082733 | 10/2003 |
| WO | WO 2006/048531 | 5/2006 |
| WO | WO-2006/080702 A1 | 8/2006 |
| WO | WO 2006/115486 | 11/2006 |
| WO | WO 2007/015710 | 2/2007 |
| WO | WO 2007/061854 | 5/2007 |
| WO | WO 2007/089118 | 8/2007 |
| WO | WO 2007/149109 | 12/2007 |
| WO | WO 2008/012196 | 1/2008 |
| WO | WO-2008/035730 A1 | 3/2008 |
| WO | WO 2008/041183 | 4/2008 |

(56) References Cited

FOREIGN PATENT DOCUMENTS

| WO | WO-2008/054409 A2 | 5/2008 |
|---|---|---|
| WO | WO 2008/054541 | 5/2008 |
| WO | WO 2008/085634 | 7/2008 |
| WO | WO-2008085550 A2 | 7/2008 |
| WO | WO 2008/115168 | 9/2008 |
| WO | WO 2008/115640 | 9/2008 |
| WO | WO-2008/133299 A1 | 11/2008 |
| WO | WO 2008/145787 | 12/2008 |
| WO | WO 2009/004346 | 1/2009 |
| WO | WO 2009110885 | 9/2009 |
| WO | WO-2009/125421 A1 | 10/2009 |

OTHER PUBLICATIONS

Rebouillat et al. Measuring the Electrical Conductivity of Single Fibres, Int. J. Electrochem. Sci., 6 (2011) 5731-5740.*

Park et al. Strain-dependent electrical resistance of multi-walled carbon nanotube/polymer composite films, Nanotechnology 19 (2008) 055705, pp. 1-7.*

Garcia, et al., "Fabrication and multifunctional properties of a hybrid laminate with aligned carbon nanotubes grown In Situ", Composites Science and Technology, Jul. 1, 2008, pp. 2034-2041, vol. 68, No. 9.

Ago, et al., "Colloidal Solution of Metal Nanoparticles as a Catalyst for Carbon Nanotube Growth", Proceedings Materials Research Society, Fall 2000, pp. A13.18.1-A13.18.5, vol. 633, Materials Research Society.

Andrews, et al., "Nanotube Composite Carbon Fibers," Applied Physics Letters, Aug. 1999, vol. 75, No. 9, pp. 1329-1331.

Arepalli, et al., "Carbon-Nanotube-Based Electrochemical Double-Layer Capacitor Technologies for Spaceflight Applications," JOM, Dec. 2005, pp. 26-31.

Bradford, et al., "Electrical Conductivity Study of Carbon nanotube Yarns, 3-D Hybrid Braids and their Composites", Jouranl of Composite Materials, pp. 1533-1545, vol. 42, No. 15, SAGE Productions, Los Angeles, London, New Delhi and Singapore.

Bubert, et al., "Basic analytical investigation of plasma-chemically modified carbon fibers", Spectrochimica Acta Part B., 2002, pp. 1601-1610, vol. 57, Elsevier Science B.V.

Chae, et al., "A comparison of reinforcement efficiency of various types of carbon nanotubes in polyacrylonitrile fiber", Polymer, Nov. 21, 2005, pp. 10925-10935, vol. 46, No. 24, Elsevier Ltd.

Che, et al., "Chemical Vapor Deposition Based Synthesis of Carbon Nanotubes and Nanofibers Using a Template Method", Chem. Mater., 1998, pp. 260-267, vol. 10, American Chemical Society.

Chen, et al., "Basalt fiber-epoxy laminates with functionalized multi-walled carbon nanotubes", Composites, Part A, 2009, pp. 1082-1089, vol. 40, Elsevier Ltd.

Chen, et al., "Pulsed electrodeposition of Pt nanoclusters on carbon nanotubes modified carbon materials using diffusion restricting viscous electroyles", Electrochemistry Communications, Jun. 2007, pp. 1348-1354, vol. 9, Elsevier B.V.

Ci, et al., "Direct Growth of Carbon Nanotubes on the Surface of Ceramic Fibers", Carbon, 2005, pp. 883-886, vol. 43, No. 4, Elsevier Ltd.

Cui, et al., "Carbon—Silicon Core-Shell Nanowires As High Capacity Electrode For Lithium Ion Batteries," American Chemical Society, vol. xx, No. x.

Franz, et al., "Carbon Single-Wall Nanotube Growth in a Volumetrically Confined Arc Discharge System", U.S. Departement of Energy Journal of Undergraduate Research, pp. 66-69, publication date unknown.

Garcia, et al., "Aligned Carbon Nanotube Reinforcement of Advanced Composite Ply Interfaces," 49th AIAA/ASCE/AHS/ASC Structures, Structural Dynamics, and Materials Conference, Apr. 7-10, 2008, Schaumburg, IL, MIT, American Institute of Aeronautics and Astronautics, Inc.

Hsieh, et al., "Synthesis of Carbon Nanotubes on Carbon Fabric for Use as electrochemical Capacitor," Microporous and Mesoporous Materials, (2009), pp. 155-159, vol. 122.

Hsu, et al., "Optical Absorption and Thermal Transport of Individual Suspended Carbon Nanotube Bundles", Nano Lett., 2009, pp. 590-594, vol. 9, No. 2, American Chemical Society, Publication Date (Web): Jan. 13, 2009.

Jiang, et al., "Carbon nanotube-coated solid-phase microextraction metal fiber based on sol-gel technique", Journal of Chromatography A., May 29, 2009, pp. 4641-4647, vol. 1216, Elsevier B.V.

Jiang, et al., "Plasma-Enhanced Deposition of Silver Nanoparticles onto Polymer and Metal Surfaces for the Generation of Antimicrobial Characteristics", Journal of Applied_Polymer Science, 2004, pp. 1411-1422, vol. 93, Wiley Periodicals, Inc.

Jo, et al., "Field Emission of Carbon Nanotubes Grown on Carbon Cloth," Applied Physics Letters, Aug. 2, 2004, pp. 810-812, vol. 85, No. 5.

Jung, et al., "Fabrication of radar absorbing structure (RAS) using GFR-nano composite and spring-back compensation of hybrid composite RAS shells", Composite Structures, 2006, pp. 571-576, vol. 75, Elsevier Ltd.

Kim, et al., "Processing, characterization, and modeling of carbon nanotube-reinforced multiscale composites," Composites Science and Technology, 2009, pp. 335,342, vol. 69, Elsevier Ltd.

Kind, et al., "Patterned Films of Nanotubes Using Microcontact Printing of Catalysts", Adv. Mater., 1999, pp. 1285-1289, vol. 11, No. 15, Wiley-VCH Verlag GmbH, D-69469 Weinheim.

Kramer, et al., Constrained Iron Catalysts for Single-Walled Carbon Nanotube Growth?, Langmuir 2005, 21, 8466-8470 [http://pubs.acs.org/doI/abs/10.1021/la0506729].

Laachachi, et al., "A chemical method to graft carbon nanotubes onto a carbon fiber", Materials Letters, 2008, pp. 394-397, vol. 62, Elsevier B.V.

Lee, "Syntheses and properties of fluorinated carbon materials", Journal of Fluorine Chemistry, 2007, pp. 392-403, vol. 128, Elsevier B.V.

Lee, et al., "Fabrication and design of multi-layered radar absorbing structures of MWNT-filled glass/epoxy plain-weave composites", Composite Structures, 2006, pp. 397-405, vol. 76, Elsevier Ltd.

Li, et al., "A Miniature glucose/$O_2$ biofuel cell with single-walled carbon nanotubes-modified carbon fiber microelectrodes as the substrate", Electrochemistry Communications, Jun. 2008, pp. 851-854, vol. 10, Elsevier B.V.

Li, et al., "Electromagnetic Interference (EMI) Shielding of Single-Walled Carbon Nanotube Epoxy Composites", Nano Lett., 2006, pp. 1141-1145, vol. 6, No. 6, American Chemical Society.

Makris, et al., "Carbon Nanotubes Growth and Anchorage to Carbon Fibres", Carbon Nanotubes, 2006, pp. 57-58, vol. 222, Springer, the Netherlands.

Meyyappan, et al., "Carbon nanotube growth by PECVD: a review", Plasma Sources Sci. Technol., 2003, pp. 205-216, vol. 12, IOP Publishing Ltd, UK.

Mylvaganam, "Fabrication and Application of Polymer Composites Comprising Carbon Nanotubes", Recent Pat Nanotechnol., 2007, pp. 59-65, vol. 1, Bentham Science Publishers, Ltd.

Panhuis, et al., "Carbon Nanotube Mediated Reduction in Optical Activity in Polyaniline Composite Materials", J. Phys. Chem. C, 2008, pp. 1441-1445, vol. 112, American Chemical Society.

Parrish, "Carbon Nanotubes and Carbon Layer Nanostructured Composites Grown in Improved Process," Capella University, Before It's News, Jul. 9, 2010.

Pisco, et al., "Hollow fibers integrated with single walled carbon nanotubes: Bandgap modification and chemical sensing capability", Sensors and Actuators B, 2008, pp. 163-170, vol. 129, Elsevier B.V.

Račkauskas "Carbon nanotube growth and use in energy sector", Energetika, 2006, pp. 43-46, vol. 2.

Satishkumar, et al., "Bundles of aligned carbon nanotubes obtained by the pyrolysis of ferrocene-hydrocarbon mixtures: role of the metal nanoparticles produced in situ", Chemical Physics Letters, 1999, pp. 158-162, vol. 307, Elsevier Science B.V.

Suh, et al., "Highly ordered two-dimensional carbon nanotube arrays", Applied Physics Letters, Oct. 4, 2002, pp. 2047-2049, vol. 75, No. 14, American Institute of Physics.

Thostenson et al., "Carbon Nanotube Networks: Sensing of distributed Strain and Damage for Life Prediction and Self Healing," Advanced Materials, Oct. 2, 1006, vol. 18, Iss. 21, pp. 2837-2841.

(56) References Cited

OTHER PUBLICATIONS

Wang, et al., "Penetration depth of atmospheric pressure plasma surface modification into multiple layers of polyester fabrics", Surface and Coatings Technology, 2007, pp. 77-83, vol. 202, Elsevier B.V.

Wang, et al., "Processing and property investigation of single-walled carbon nanotube (SWNT) buckypaper/epoxy resin matrix nanocomposites", Composites: Part A, 2004, pp. 1225-1232, vol. 35, Elsevier Ltd.

Wichmann, et al., "Glass-fibre-reinforced composites with enhanced mechanical and electrical properties—Benefits and limitations of a nanoparticle modified matrix", Engineering Fracture Mechanics, 2006, pp. 2346-2359, vol. 73, Elsevier Ltd.

Xu, et al., "Bone-Shaped Nanomaterials for Nanocomposite Applications", Nano Lett., 2003, pp. 1135-1139, vol. 3, No. 8, American Chemical Society.

Yabe, et al., Synthesis of well-aligned carbon nanotubes by radio frequency plasma enhanced CVD method, Diamond and Related Materials, 2004, pp. 1292-1295, vol. 13, Elsevier B.V.

Yanagishita, et al., "Carbon Nanotubes with a Triangular Cross-section, Fabricated Using Anodic Porous Alumina as the Temple", Adv. Mater., 204, pp. 429-432, vol. 16, No. 5, Wiley-VCH Verlag GmbH & Co. KGaA, Weinheim.

Yang, et al., "Electrical Conductivity and Electromagnetic Interference Shielding of Multi-walled Carbon Nanotube Filled Polymer Composites" Mater. Res. Soc. Symp. Proc., 2005, pp. HH5.3.1-HH.5.3.5, vol. 858E, Materials Research Society.

Yeh, et al., "Mechanical properties of phenolic-based nanocomposites reinforced by multi-walled carbon nanotubes and carbon fibers", Composites: Part A, 2008, pp. 677-684, vol. 39, No. 4.

Zhang et al., "Integration and characterization of aligned carbon nanotubes on metal/silicon substrates and effects of water", Applied Surface Science 255 (2009) 5003-5008, entire document.

Zhang, et al., "In situ growth of carbon nanotubes on inorganic fibers with different surface properties," Materials Chemistry and Physics, 2008, pp. 317-321, vol. 107, Science Direct.

Zhao et al., "The Use of Carbon Nanotubes to Sense Matrix Stresses Around a Single Glass Fiber," Composites Science and Technology, Nov. 2001, vol. 61, No. 14, pp. 2139-2143.

Zhao, et al., "Carbon Nanosheets as the Electrode Material in Supercapacitors," Journal of Power Sources 194 (2009 pp. 1208-1212.

Zhao, et al., "Growth of carbon nanotubes on the surface of carbon fibers", Carbon, 2007, pp. 380-383, vol. 46, No. 2, Elsevier Ltd.

Zhao, et al., "The growth of multi-walled carbon nanotubes with different morphologies on carbon fibers", Carbon, 2005, pp. 651-673, vol. 43, Elsevier Ltd.

Zhu, et al., "Carbon nanotube growth on carbon fibers", Diamond and Related Materials, 2003, pp. 1825-1825, vol. 12, Elsevier B.V.

Zhu, et al., "Synthesis of single-walled carbon nanotubes by the vertical floating catalyst method," Chinese Science Bulletin, 2002, pp. 159-162, vol. 47, No. 2.

Hou et al., "A resistance-based damage location sensor for carbon-fibre composites", Smart Materials and Structures, Nov. 4, 2002, vol. 11, pp. 966-969.

Thostenson et al., "Real-time in situ sensing of damage evolution in advanced fiber composites using carbon nanotube networks", Nanotechnology, Apr. 23, 2008, vol. 19.

Buehler GmbH, Safety Data Sheet 1907/2006/EC (GB) Buehler EpoThin Hardener, revised Apr. 21, 2008, 5 pages.

Buehler GmbH, Safety Data Sheet 1907/2006/EC (GB) Buehler EpoThin Resin, revised Apr. 21, 2008, 5 pages.

CRC Handbook of Chemistry and Physics, $95^{th}$ Edition, 2014-2015, Physical Constants of Inorganic Compounds, p. 4-45.

The University of Edinburgh School of GeoSciences, Sample Preparation Procedures, revised Aug. 23, 2008, 6 pages.

Fiedler et al, "Can Carbon Nanotubes Be Used to Sense Damage in Composites?", Annales de Chimie—Science des Materiaux, 2004, vol. 29, No. 6, pp. 81-94.

vanSchalkwijk, et al., "Advances in Lithium-Ion Batteries," Kluwer Academic Plenum Publishers, 2002, p. 499.

Ma, et al., "Electrochemical properties of manganese oxide coated onto carbon nanotubes for energy-storage applications," Dec. 2007, Journal of Power Sources, pp. 483-489, vol. 178, No. 1.

Lee, et al., "Fabrication of polypyrrole (PPy)/carbon nanotube (CNT) composite electrode on ceramic fabric for supercapacitor applications," Jun. 2011, Electrochimica ACTA, pp. 7460-7466, vol. 56, No. 22.

Stoller, et al., "Best practice methods for determining an electrode material's performance for ultracapacitors," Jan. 2010, Energy & Environmental Science, pp. 1294-1301, vol. 3, No. 9.

CRC Handbook of Chemistry and Physics, 95th Edition, 2014-2015, Physical Constants of Inorganic Compounds, p. 4-88.

\* cited by examiner

RESISTANCE MEASUREMENT SYSTEM AND METHOD OF USING THE SAME

BACKGROUND

The present invention relates to systems and methods used in the manufacture of carbon nanostructure-laden materials, and more specifically to measuring the resistance of carbon nanostructure-laden materials during their manufacture.

High-performance materials incorporating carbon nanostructures (CNSs) are becoming increasingly important industrially. CNSs may impart desirable properties to composites, for example, such as enhanced mechanical strength, and thermal and electrical conductivity. The small diameter and robust individual carbon-carbon bonds of carbon nanotubes (CNTs), in particular, provide stiffness, strength, and thermal conductivity which exceed most known natural and synthetic materials.

In order to harness these properties, a continuing challenge has been to reliably incorporate CNTs and other CNSs into various structures, preferably in a controlled and ordered fashion. While the preparation of CNTs, in particular, has been successfully scaled up, employing loose CNTs has been problematic due, at least in part, to their tendency to agglomerate. Moreover, when combined in a typical matrix material, CNT loading can be severely limited by the concomitant increases in viscosity, ultimately putting an upper limit on the amount of CNTs that can be placed in the matrix material. As a consequence, there has been increased interest in the preparation of CNTs on various substrates as scaffolds to pre-organize the CNTs and to allow access to higher CNT loadings.

As the means for synthesizing CNSs, such as CNTs, on a variety of substrates begins to mature and industrial scale up begins to take hold, it will be beneficial to put into place measures to ensure quality control of the materials being prepared. Although there are means for analyzing CNT loading of a substrate, there are no real-time quantitative evaluations adapted for in-line use. CNT loading evaluation methods include, for example, thermogravimetric analysis employing CNT burnoff, measuring mass per unit length, and the use of scanning electron microscope (SEM) techniques. Currently, such evaluations are done "offline," that is, after the material is prepared and via random sampling.

Thermogravimetric analysis employs random sampling and destroys the very substrate being prepared. Measuring mass per unit length provides only an averaged evaluation of loading over an entire stretch of substrate and is difficult to employ real-time and fails to identify regions that may not be up to quality standards. Similarly, SEM techniques are inadequate for large scale quality control assurance, because only random samplings of the CNS-laden substrate are evaluated. Each of these post synthesis analyses may be inadequate to detect problems that may occur, for example, during a long synthesis run. Moreover, the use of CNS-laden materials that may have undesirable imperfections, such as regions of poor CNS coverage, may be catastrophic under high stress conditions of certain downstream applications.

SUMMARY OF THE INVENTION

The present invention relates to systems and methods used in the manufacture of carbon nanostructure-laden materials, and more specifically to measuring the resistance of carbon nanostructure-laden materials during their manufacture.

In some embodiments, the present invention provides a quality control system for the manufacture of carbon nanostructure (CNS)-laden substrates comprising a resistance measurement module for continuously measuring the resistance of the (CNS)-laden substrate.

In some embodiments, the present invention provides a method comprising continuously synthesizing carbon nanostructures (CNSs) on a substrate in a CNS growth chamber to provide a CNS-laden substrate and continuously monitoring the resistance of the CNS-laden substrate exiting a distal end of the growth chamber.

The features and advantages of the present invention will be readily apparent to those skilled in the art upon a reading of the description of the various embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to those skilled in the art and having the benefit of this disclosure.

DETAILED DESCRIPTION

The present invention relates to systems and methods used in the manufacture of carbon nanostructure-laden materials, and more specifically to measuring the resistance of carbon nanostructure-laden materials during their manufacture. In particular, embodiments disclosed herein provide a means of assessing the quality of CNS-laden substrates in real time. That is, the systems and methods employed in various embodiments allow for integration of a quality assessment system in-line as part of the CNS preparation process. This may be accomplished via a resistance measurement module that continuously measures the resistance of a moving substrate onto which CNS structures are being synthesized. Advantageously, when run in real-time in a continuous mode during CNS preparation, feedback mechanisms are readily incorporated and such feedback is reportable to an operator, other instrumentation (such as a CNS growth chamber/module), or both, so that the synthesis conditions may be altered, or, as necessary, operations halted.

Although beneficial to run such assessments in real-time, the resistance measurement module disclosed herein can also stand alone and can be useful for evaluating bulk quantities of materials that may have been prepared elsewhere. This is readily accomplished by independently running the CNS-laden substrate through the resistance measurement module, for example, in a simple spool to spool arrangement with the intervening resistance measurement module. Thus, the evaluation of CNS loading need not be limited to real-time evaluation during synthesis.

The systems and methods disclosed herein are sufficiently versatile that they can be used to evaluate CNS loading values for CNSs grown on a variety of substrates. Systems and methods disclosed herein are particularly well-suited to evaluating CNS growth on fibrous substrates, including, without limitation, carbon, glass, quartz, ceramic, aramids, such as Kevlar, basalt, and metal fibers. Metallic substrates may include, without limitation, aluminum, copper, and steel, for example. Fibrous substrates can take on numerous forms including, without limitation, fibers, tows, yarns, fabrics, tapes, and the like. Other forms, which may be common for metallic substrates include, without limitation plates, foils, thin films, meshes, wires, and the like.

Figure 1:
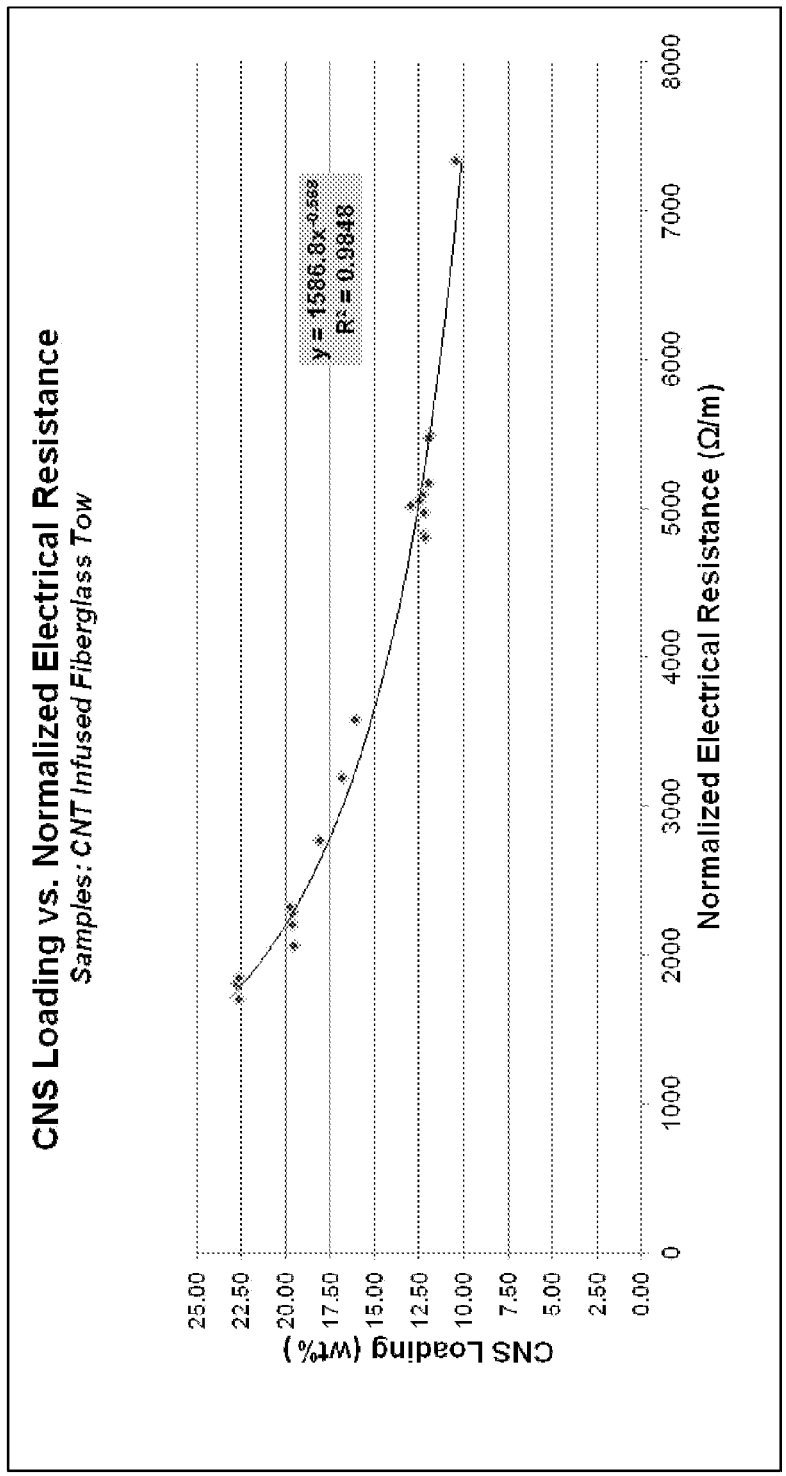
FIG. 1 shows a plot correlating carbon nanostructure loading with substrate resistance for CNS-infused fiberglass tow in a range in which about 10 percent to about 25 percent of the fiber weight consisted of CNS.

Without being bound by theory, the presence of CNSs on a substrate, regardless of the substrate type, can alter the resistance of the substrate. Such alteration in resistance can be observed for non-conductive substrates such as glass fiber for which the substrate is altered from being electrically insulating to being a conductor as CNS loading is increased. That is, the resistance of the substrate decreases with increased in CNS loading. Such a correlation between CNS loading and resistance has been demonstrated as indicated in FIG. 1.

Similar correlations hold for electrically conductive substrates such as carbon fiber for which the substrate may have a bulk conductivity greater than the CNSs grown thereon. In some such embodiments, the resistance may actually increase with increased CNS loading. Regardless of the substrate, the presence of CNSs on a substrate can alter the resistance value and thus, provides a means for correlation to a CNS loading value.

Finally, methods and systems disclosed herein offer the ability to capture CNS loading values on a moving substrate without stopping the line, providing both quality assurance and reduced production times. Data can be collected at very high acquisition rates with multiple readings per second. The systems and methods can be utilized independently of the linespeed of operation, whether the line is moving, for example, at 100 ft/min, 1 ft/min or even if the line has been temporarily stopped i.e. 0 ft/min. During long synthesis runs, methods and systems disclosed herein have the ability to detect changes in loading in real-time continuously throughout a given run providing a means for assessing consistency of CNS growth on manufacturing scale.

As used herein, the term "linespeed" refers to the speed at which a substrate of spoolable dimensions can be fed through the CNS infusion processes described herein, where linespeed is a velocity determined by dividing CNS chamber(s) length by the material residence time.

As used herein the term "spoolable dimensions" refers to fiber, ribbon, tapes, sheet, mesh and similar materials having at least one dimension that is not limited in length, allowing for the material to be stored on a spool or mandrel. Materials of "spoolable dimensions" have at least one dimension that indicates the use of either batch or continuous processing for CNS infusion as described herein. Commercial fiber roving, in particular, can be obtained on 1 oz, ¼, ½, 1, 5, 10, 25 lb, and greater spools, for example. Processes of the invention operate readily with 1 to 25 lb. spools, although larger spools are usable. Moreover, a pre-process operation can be incorporated that divides very large spoolable lengths, for example 100 lb. or more, into easy to handle dimensions, such as two 50 lb spools.

As used herein, the term "carbon nanostructure" (CNS, plural CNSs) refers to a nanostructured carbon network that includes elements of carbon nanotube structure in a complex morphology which can include any combination of branching, entanglement, and the like, while still providing typical mechanical, thermal, and electrical properties to substrates on which they are infused.

As used herein, the term "carbon nanotube" (CNT, plural CNTs) refers to any of a number of cylindrically-shaped allotropes of carbon of the fullerene family including single-walled carbon nanotubes (SWNTs), double-walled carbon nanotubes (DWNTS), multi-walled carbon nanotubes (MWNTs). CNTs can be capped by a fullerene-like structure or open-ended. CNSs include those that encapsulate other materials.

As used herein, the term "carbon nanostructure (CNS)-laden substrate" refers to any substrate onto which carbon nanostructures have been infused.

As used herein, the term "infused" means bonded and "infusion" means the process of bonding. Such bonding can involve direct covalent bonding, ionic bonding, pi-pi, and/or van der Waals force-mediated physisorption. For example, CNSs may be infused directly to the substrate whose resistance is to be measured.

As used herein, the term "material residence time" refers to the amount of time a discrete point along a substrate of spoolable dimensions is exposed to CNS growth conditions during the CNS infusion processes described herein. This definition includes the residence time when employing multiple CNS growth chambers.

Figure 2:
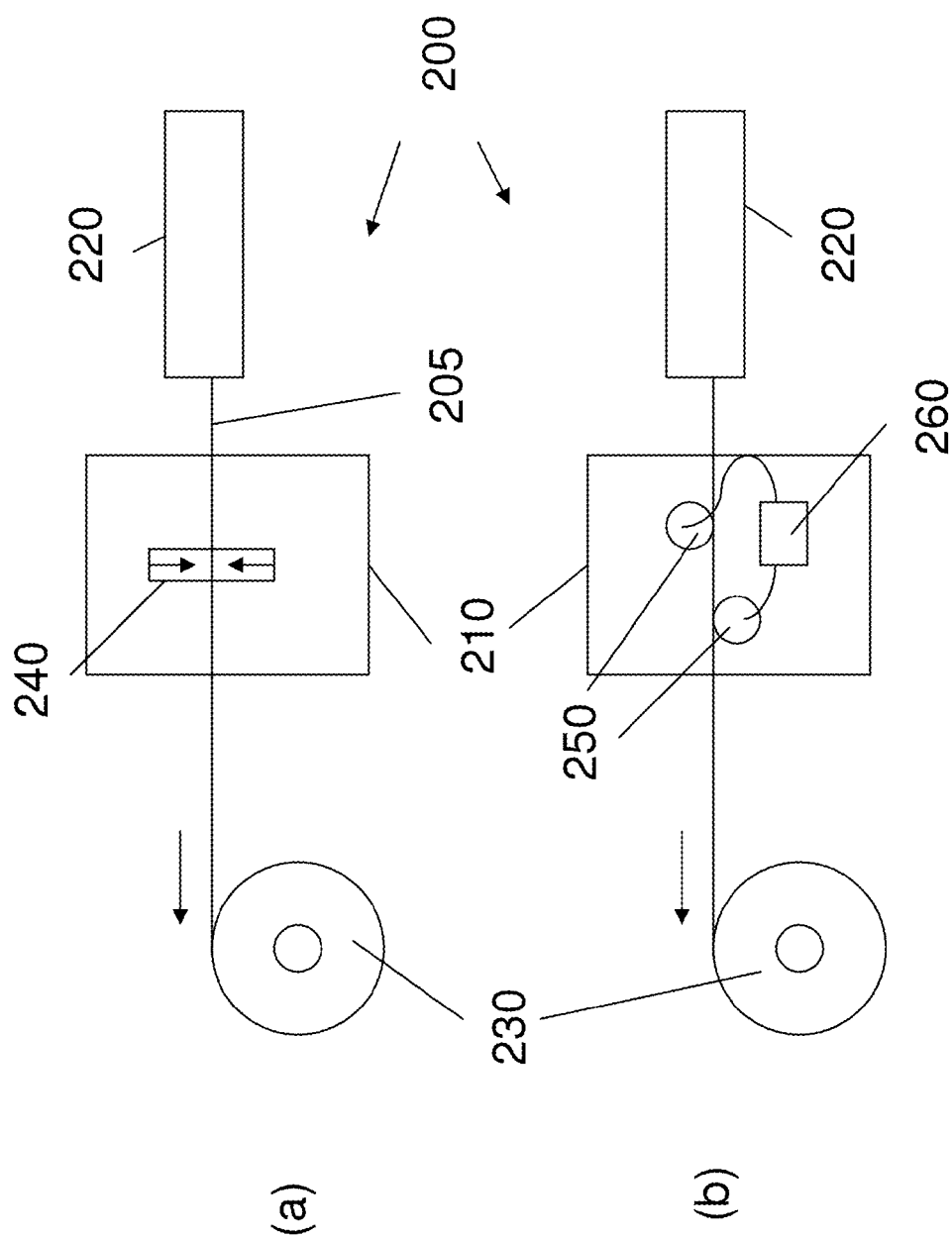
FIG. 2a shows a system comprising a resistance measurement module comprising an electric field- or inductive-based device for measurement of resistance.
FIG. 2b shows a system comprising a resistance measurement module comprising a conducting rollers linked to a resistance measurement device.

In some embodiments, the present invention provides a quality control system for the manufacture of carbon nanostructure-laden substrates comprising a resistance measurement module for continuously measuring resistance of the carbon nanostructure (CNS)-laden substrate. In some embodiments, the resistance measurement module measures resistance via an electric field or inductive based measurement. Referring now to FIG. 2($a$), there is shown a system 200 having a resistance module 210 configured to received a substrate 205 from a source 220. After measurement of resistance via an electric field or inductive based measurement via device 240 within resistance measurement module 210, substrate 205 is delivered to a take-up spool or mandrel 230. Source 220 can be any supply of a substrate for which resistance measurement is desired. In some embodiments source 220 is a CNS growth chamber. In other embodiments, source 220 is another spool or other holding source for delivery of substrate 205 to resistance measurement module 210. In some embodiments, source 220 can house any substrate 205 for which measurement of resistance is desired and substrate 205 need not be limited to CNS-laden substrates. In the configuration of FIG. 2$a$, device 240 may supply an electric or magnetic field of known strength across a length of substrate 205, inducing a current in substrate 205. In some such embodiments, device 240 may comprise a current clamp. Measurement of the induced current and voltage allows calculation of resistance according to Ohm's law $V=IR$.

As shown in FIG. 2($b$), in some embodiments, resistance measurement module 210 comprises at least a two point conductive contact 250 with CNS-laden substrate 205. In use, substrate 205 is delivered to resistance measurement module 210 and at least a two point contact 250 is electronically linked to a resistance measurement device 260, such as an ohmmeter to provide real time measurement across a fixed length of substrate 205. In some embodiments, the length between at least two contact points can be selected by the operator. In some embodiments, the resistance measurement module 210 can be configured with movable conductive contacts 250, relative to each other, so that the length over which resistance is measured can be changed. In some such embodiments, alteration in the length can be performed manually, while in other embodiments, the length can altered in conjunction with a computer-assisted interface. In yet still further embodiments, the length between conductive contacts 250 can be programmed. In some embodiments, the length over which resistance is measured can be in a range from about 1 millimeter to about 1 meter. One skilled in the art will appreciate that shorter lengths between conductive contacts 250 may provide more variability in the resistance measurements as a function of time. Likewise, at larger lengths between conductive contacts 250, the variability may be smaller as the resistance being measured approaches the average of the bulk material and imperfections may be averaged out. In some embodiments, therefore, it may be desirable to maintain short lengths between conductive contacts 250, such as between about 1 millimeter to about 10 cm.

Figure 5:
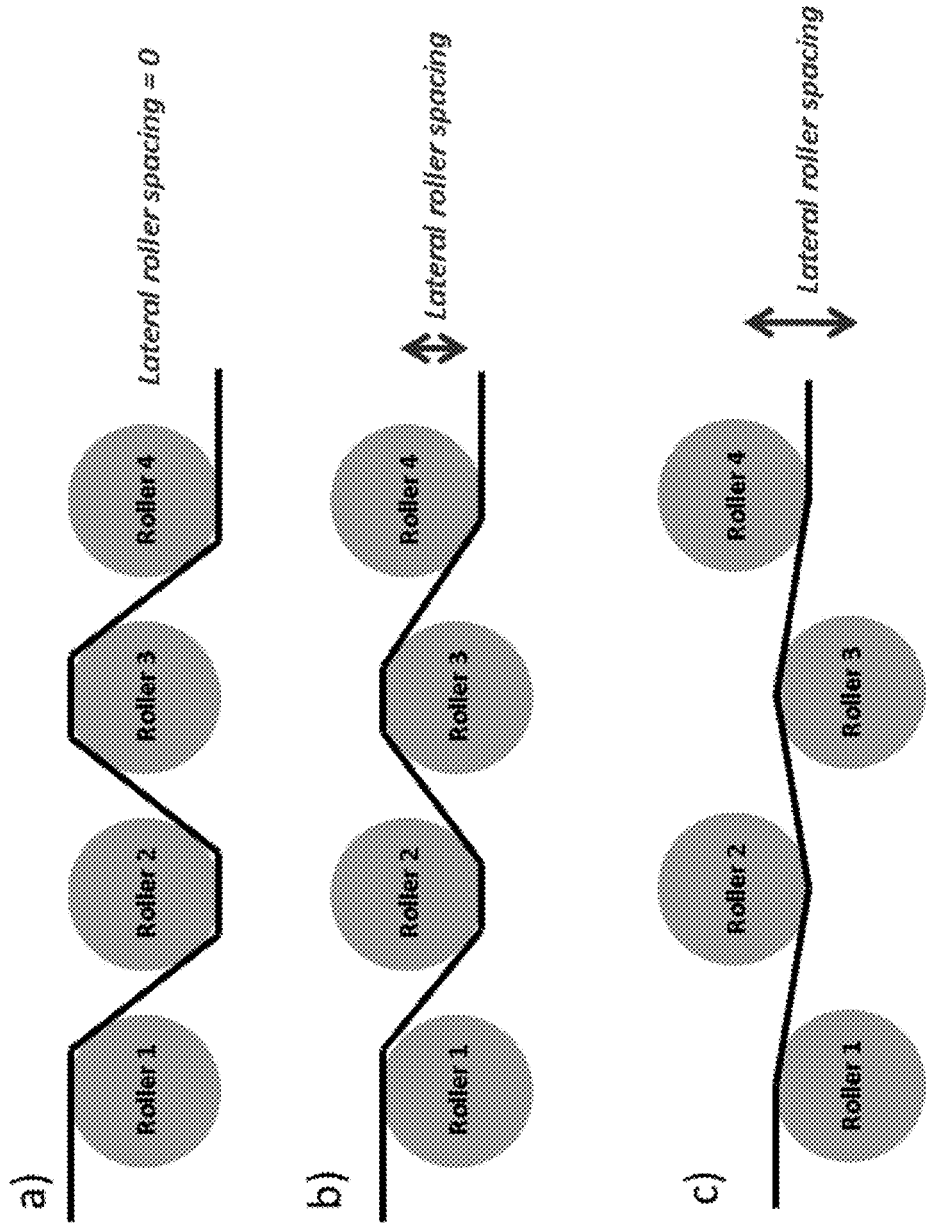
FIG. 5a-c show the four roller system of FIG. 4a having variable lateral spacing of the conductive rollers, in accordance with embodiments disclosed herein.

In some embodiments, spacing between contacts both vertically (i.e. laterally, see roller examples in FIG. 5) and horizontally are used to modulate the tension of the substrate as it goes over the contact points in order to optimize the resistance measurement. The tension can thus be regulated during winding of the substrate as it passes from source 220 to take up spool or mandrel 230.

In some embodiments, conductive contacts 250 can be configured to move along substrate 205. In some such embodiments, substrate 205 may be stationary. In other embodiments conductive contacts 250 can be configured to move along substrate 205 which is in motion. In some such embodiments, the direction of the moving conductive contacts 250 may be against the direction of the movement of substrate 205. In some embodiments, conductive contacts 250 may be configured to scan back and forth along substrate 205 while it is in motion. In some embodiments, two point conductive contact 250 can comprise a pair of conducting rollers that are configured to accept substrate 205, for example in a groove.

In some embodiments, system 200 of FIGS. 2a may comprise additional modules between source 220 and resistance measurement module 210 and/or additional modules between resistance measurement module 210 and take-up spool 230. For example, additional materials may be introduced onto substrate 205 before or after proceeding through resistance measurement module. Such additional materials can include, without limitation, sizing agents, coatings, lubricants, surfactants, antistatic agents, other conducting elements, and the like, the exact nature of which may depend on the particular downstream application for substrate 205. In some embodiments, substrate 205 can also undergo physical alteration prior to or after passing through resistance measure module 210. For example, in some embodiments, where the CNSs comprises substantially CNTs, the CNTs may be oriented in an electric field. Depending on the form of substrate 205, other alterations may be performed prior to or after resistance measurement. For example, a tow material may be spread or fibers that exit the source in a spread form may be re-bundled.

In some embodiments, system 200 of FIGS. 2a and 2b may be equipped with more than one resistance measurement module 210. For example, system 200 may comprise two, three, or four resistance measurement modules 210. Such additional resistance measurement modules 210 may be disposed before or after any additional substrate 205 altering modules as described above.

Figure 3:
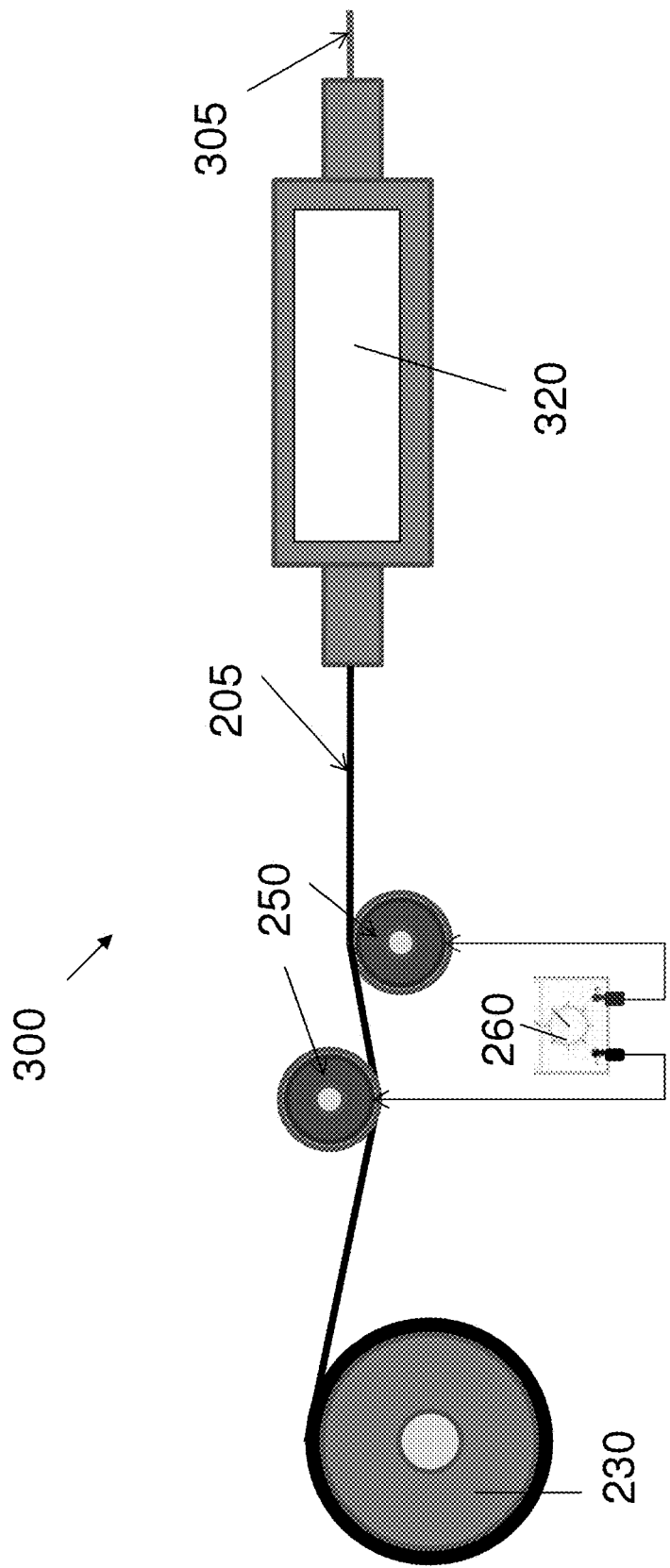
FIG. 3 shows a system comprising a resistance measurement module in the context of a continuous CNS growth process.
Figure 4:
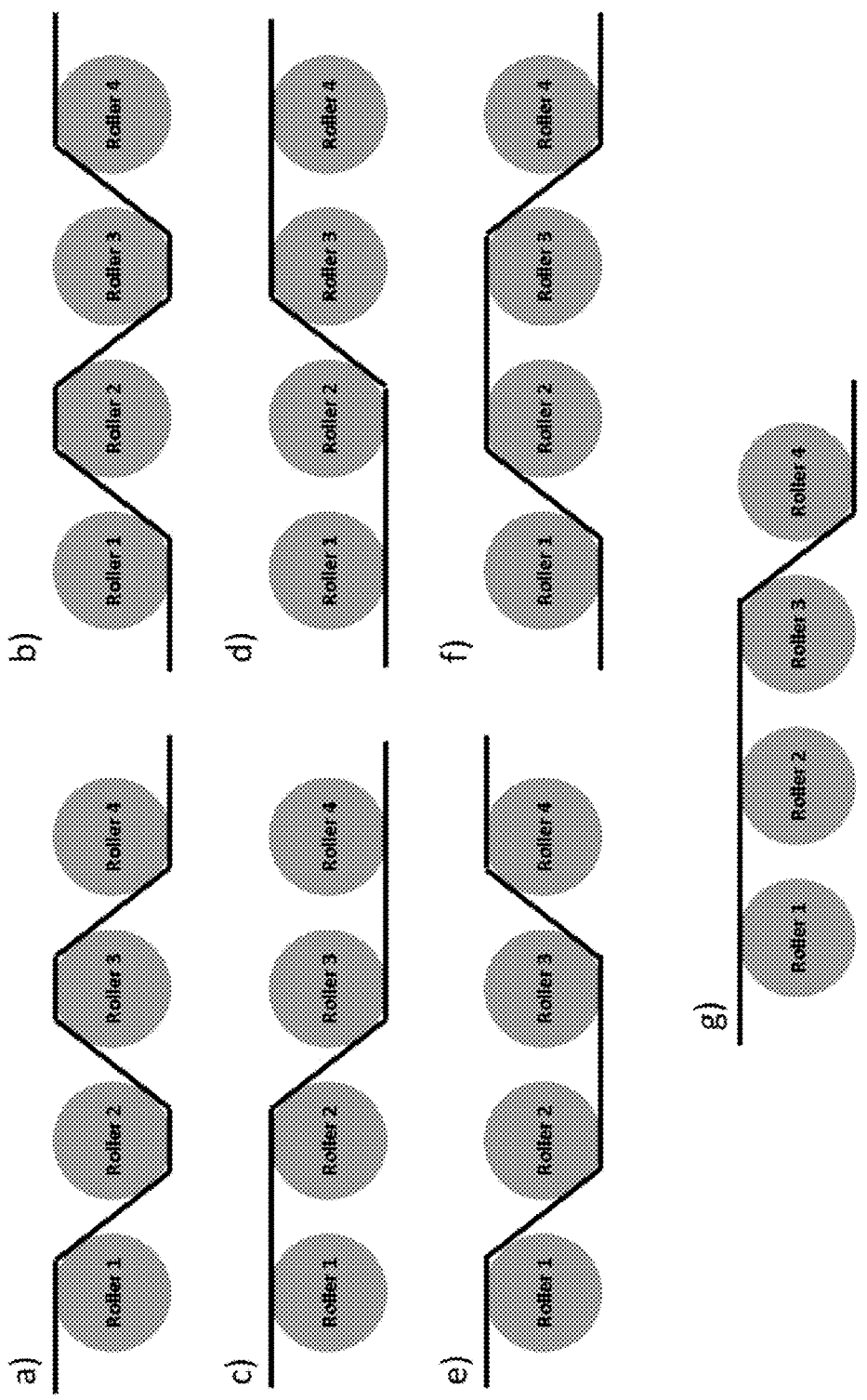
FIGS. 4a-g show exemplary embodiments of a system employing four conductive rollers for measuring resistance of a CNS-laden substrate, in accordance with embodiments disclosed herein.

In some embodiments, the CNS-laden substrate is fed continuously to the resistance measurement module from a CNS growth module, the CNS growth module itself being configured to continuously synthesize CNSs on a substrate precursor. Referring now to FIG. 3, there is shown an exemplary configuration of this embodiment. System 300 includes a CNS growth chamber 310 which receives a precursor substrate 305, which is typically catalyst-laden. CNS synthesis occurs in chamber 310, to provide CNS-laden substrate 205 at its distal end. Substrate 205 can be directly delivered to resistance measurement module 210 and taken up on take-up spool 230, as described herein. CNS growth chambers 310 and methods for synthesizing CNS-laden substrates 205 have been described in detail in related pending published U.S. Patent Application Nos. 2010/0276072, 2010/0279569, 2011/0168083, 2011/0168089, 2011/0171469, 2010-0272891, the relevant portions of which are incorporated herein by reference.

The following description is provided as guidance to the skilled artisan for producing carbon nanostructures (CNS)-laden substrates 205 in growth chamber 320. It will be recognized by those skilled in the art, that embodiments describing the preparation of carbon nanostructures on substrates disclosed below are merely exemplary. It is to be understood that the forgoing discussion uses the terms carbon nanostructure (CNS) and carbon nanotubes (CNT) interchangeably, as the exact nature of the CNS product is complex, but has as it primary structural element the carbon nanotube.

In some embodiments, the present invention utilizes fiber tow materials as pre-cursor substrate 305. The processes described herein allow for the continuous production of CNSs of uniform length and distribution along spoolable lengths of tow, roving, tapes, fabrics, meshes, perforated sheets, solid sheets, and ribbons. While various mats, woven and non-woven fabrics and the like can be functionalized by processes of the invention, it is also possible to generate such higher ordered structures from the parent roving, tow, yarn or the like after CNS functionalization of these parent materials. For example, a CNS-infused chopped strand mat can be generated from a CNS-infused fiber roving. As used herein the term "substrate" refers to any material which has fiber as its elementary structural component. The term encompasses, fibers, filaments, yarns, tows, tapes, woven and non-woven fabrics, plies, mats, and meshes.

Compositions having CNS-laden substrates are provided in which the CNSs may be substantially uniform in length. In the continuous process described herein, the residence time of the substrate in a CNS growth chamber can be modulated to control CNS growth and ultimately, CNS length. This provides a means to control specific properties of the CNSs grown. CNS length can also be controlled through modulation of the carbon feedstock and carrier gas flow rates, and growth temperature. Additional control of the CNS properties can be obtained by controlling, for example, the size of the catalyst used to prepare the CNSs. For example, 1 nm transition metal nanoparticle catalysts can be used to provide SWNTs in particular. Larger catalysts can be used to prepare predominantly MWNTs.

Additionally, the CNS growth processes employed are useful for providing CNS-laden substrate 205 with uniformly distributed CNSs on substrates while avoiding bundling and/or aggregation of the CNSs that can occur in processes in which pre-formed CNSs are suspended or dispersed in a solvent solution and applied by hand to the substrate. Such aggregated CNSs tend to adhere weakly to a substrate and the characteristic CNS properties are weakly expressed, if at all. In some embodiments, the maximum distribution density, expressed as percent coverage, that is, the surface area of fiber covered, can be as high as about 55%, assuming CNSs comprising CNTs with about 8 nm diameter with 5 walls. This coverage is calculated by considering the space inside the CNSs as being "fillable" space. Various distribution/density values can be achieved by varying catalyst dispersion on the surface as well as controlling gas composition, linespeed of the process, and reaction temperatures. Typically for a given set of parameters, a percent coverage within about 10% can be achieved across a substrate surface. Higher density and shorter CNSs are useful for improving mechanical properties, while longer CNSs with lower density are useful for improving thermal and electrical properties, although increased density is still favorable. A lower density can result when longer CNSs are grown. This can be the result of employing higher temperatures and more rapid growth causing lower catalyst particle yields.

The CNS-laden substrate 205 can include a substrate such as a metal filament, a fiber yarn, a fiber tow, a metal tape, a fiber-braid, a woven metal fabric, a non-woven fiber mat, a fiber ply, meshes ribbons, solid metal sheets, and perforated metal sheets. Metal filaments include high aspect ratio fibers having diameters ranging in size from between about 10 microns to about 12.5 mm or greater. Fiber tows are generally compactly associated bundles of filaments and are usually twisted together to give ropes.

Ropes include closely associated bundles of twisted filaments. Each filament diameter in a ropes is relatively uniform. Ropes have varying weights described by their 'tex,' expressed as weight in grams of 1000 linear meters, or denier, expressed as weight in pounds of 10,000 yards, with a typical tex range usually being between about 4000 tex to about 100000 tex.

Tows include loosely associated bundles of untwisted filaments. As in ropes, filament diameter in a tow is generally uniform. Tows also have varying weights and the tex range is usually between 2000 g and 12000 g. They are frequently characterized by the number of thousands of filaments in the tow, for example 10 wire rope, 50 wire rope, 100 wire rope, and the like.

Metal meshes are materials that can be assembled as weaves or can represent non-woven flattened ropes. Metal tapes can vary in width and are generally two-sided structures similar to ribbon. Processes of the present invention are compatible with CNS infusion on one or both sides of a tape. CNS-infused tapes can resemble a "carpet" or "forest" on a flat substrate surface. Again, processes of the invention can be performed in a continuous mode to functionalize spools of tape.

Fiber-braids represent rope-like structures of densely packed fibers. Such structures can be assembled from ropes, for example. Braided structures can include a hollow portion or a braided structure can be assembled about another core material.

In some embodiments, a number of primary substrate structures can be organized into fabric or sheet-like structures. These include, for example, woven metal meshes non-woven fiber mat and fiber ply, in addition to the tapes described above. Such higher ordered structures can be assembled from parent tows, ropes, filaments or the like, with CNSs already infused in the parent fiber. Alternatively such structures can serve as the substrate for the CNS infusion processes described herein.

Metals substrates can include any metal in zero-valent oxidation state including, for example, d-block metals, lanthanides, actinides, main group metals and the like. Any of these metals can also be used in non-zero-valent oxidation state, including, for example, metal oxides, metal nitrides, and the like. Exemplary d-block metals include, for example, scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and gold. Exemplary main group metals include, for example, aluminum, gallium, indium, tin, thallium, lead, and bismuth. Exemplary metal salts useful in the invention include, for without limitation, oxides, carbides, nitrides, and acetates.

CNSs useful for infusion to substrates include single-walled CNTs, double-walled CNTs, multi-walled CNTs, and mixtures thereof. The exact CNSs to be used depends on the application of the CNS-infused fiber. CNSs can be used for thermal and/or electrical conductivity applications, or as insulators. In some embodiments, the infused CNSs are single-wall nanotubes. In some embodiments, the infused CNSs are multi-wall nanotubes. In some embodiments, the infused CNSs are a combination of single-wall and multi-wall nanotubes. There are some differences in the characteristic properties of single-wall and multi-wall nanotubes that, for some end uses of the fiber, dictate the synthesis of one or the other type of nanotube. For example, single-walled nanotubes can be semi-conducting or metallic, while multi-walled nanotubes are metallic.

CNSs lend their characteristic properties such as mechanical strength, low to moderate electrical resistivity, high thermal conductivity, and the like to the CNS-laden substrate. For example, in some embodiments, the electrical resistivity of a CNS-laden substrate is lower than the electrical resistivity of a parent substrate. The infused CNSs can also provide beneficial conductivity with lighter weights. Moreover, the use of shorter CNSs can be used to provide a greater tensile strength, while also improving electrical conductivity. More generally, the extent to which the resulting CNS-laden substrate expresses these characteristics can be a function of the extent and density of coverage of the fiber by the carbon nanotubes. Any amount of the fiber surface area, from 0-55% of the fiber can be covered assuming an 8 nm diameter, 5-walled MWNT (again this calculation counts the space inside the CNTs as fillable). This number is lower for smaller diameter CNSs and more for greater diameter CNSs. 55% surface area coverage is equivalent to about 15,000 CNSs/micron2. Further CNS properties can be imparted to the substrate in a manner dependent on CNS length, as described above. Infused CNSs can vary in length ranging from between about 1 micron to about 500 microns, including 1 micron, 2 microns, 3 microns, 4 micron, 5, microns, 6, microns, 7 microns, 8 microns, 9 microns, 10 microns, 15 microns, 20 microns, 25 microns, 30 microns, 35 microns, 40 microns, 45 microns, 50 microns, 60 microns, 70 microns, 80 microns, 90 microns, 100 microns, 150 microns, 200 microns, 250 microns, 300 microns, 350 microns, 400 microns, 450 microns, 500 microns, and all values in between. CNSs can also be less than about 1 micron in length, including about 0.5 microns, for example. CNSs can also be greater than 500 microns, including for example, 510 microns, 520 microns, 550 microns, 600 microns, 700 microns and all values in between.

CNSs may have a length from about 1 micron to about 10 microns. Such CNS lengths can be useful in application to increase shear strength. CNSs can also have a length from about 5-70 microns. Such CNS lengths can be useful in application to increase tensile strength if the CNSs are aligned in the fiber direction. CNSs can also have a length from about 10 microns to about 100 microns. Such CNS lengths can be useful to increase electrical/thermal and mechanical properties. The synthesis processes employed can also provide CNSs having a length from about 100 microns to about 500 microns, which can also be beneficial to increase electrical and thermal properties. One skilled in the art will recognize that the properties imparted are a continuum and that some tensile strength benefits can still be realized at longer CNS lengths. Likewise, shorter CNS lengths can still impart beneficial electrical properties as well. Control of CNS length is readily achieved through modulation of carbon feedstock and carrier gas flow rates coupled with varying process linespeeds and reaction temperatures, as described further below.

In some embodiments, spoolable lengths of CNS-laden substrates 205 can have various uniform regions with different lengths of CNSs. For example, it can be desirable to have a first section of CNS-laden substrate with uniformly shorter CNS lengths to enhance tensile and shear strength properties, and a second section of the same spoolable material with a uniform longer CNS length to enhance electrical or thermal properties.

Processes of the invention for CNS infusion to substrates allow control of the CNS lengths with uniformity and in a continuous process allowing spoolable substrates to be functionalized with CNSs at high rates. With material residence times between 5 to 300 seconds, linespeeds in a continuous process for a system that is 3 feet long can be in a range anywhere from about 0.5 ft/min to about 36 ft/min and greater. The speed selected depends on various parameters as explained further below.

In some embodiments, a material residence time in CNS growth chamber 320 of about 5 to about 300 seconds in a CNS growth chamber can produce CNSs having a length between about 1 micron to about 10 microns. In some embodiments, a material residence time of about 30 to about 180 seconds in a CNS growth chamber can produce CNSs having a length between about 10 microns to about 100 microns. In still other embodiments, a material residence time of about 180 to about 300 seconds can produce CNSs having a length between about 100 microns to about 500 microns. One skilled in the art will recognize that these numbers are approximations and that growth temperature and carrier and carbon feedstock flow rates can also impact CNS growth for a given material residence time. For example, increased temperatures typically increase the overall growth rate requiring less material residence time for a desired CNS length. Increased carbon feedstock flow rate ratio (inert to carbon feedstock) can also increase growth rates although this effect is less than changing the growth temperature.

CNS-laden substrate 205 may optionally include a barrier coating. Such barrier coatings may facilitate CNS synthesis on particularly challenging substrate materials. For example, materials that may not directly withstand CNS synthesis temperatures, or substrates on which CNS forming catalysts may be overly mobile on the surface and cause catalyst particles to undesirably agglomerate. Barrier coatings can include, for example, an alkoxysilane, such as methylsiloxane, an alumoxane, alumina nanoparticles, spin on glass and glass nanoparticles. As described below, the CNS-forming catalyst can be added to an uncured barrier coating material and then applied to the substrate together. In other embodiments the barrier coating material can be added to the substrate prior to deposition of the CNS-forming catalyst. The barrier coating material can be of a thickness sufficiently thin to allow exposure of the CNS-forming catalyst to the carbon feedstock for subsequent CVD growth. In some embodiments, the thickness is less than or about equal to the effective diameter of the CNS-forming catalyst. In some embodiments, the thickness is between about 10 nm and about 100 nm. In some embodiments, the thickness can be less than 10 nm, including 1 nm, 2 nm, 3 nm, 4 nm, 5 nm, 6 nm, 7 nm, 8 nm, 9 nm, and any value in between.

Without being bound by theory, the barrier coating can serve as an intermediate layer between the substrate and the CNSs and serves to mechanically infuse the CNSs to the substrate via a locked CNS-forming catalyst nanoparticle that serves as a site CNS growth. Such mechanical infusion provides a robust system in which the substrate serves as a platform for organizing the CNSs while still imparting properties of the CNSs to the substrate. Moreover, the benefit of including a barrier coating is the immediate protection it provides the substrate from chemical damage due to exposure to moisture, oxygen and any thermal effects of alloying, sintering, or the like when heating the substrate at the temperatures used to promote CNS growth.

In some embodiments the present invention provides a continuous process for CNS infusion that includes (a) disposing a carbon nanotube-forming catalyst on a surface of a substrate of spoolable dimensions; and (b) synthesizing carbon nanostructures directly on the substrate, thereby forming a CNS-laden substrate. For a 9 foot long system, the linespeed of the process can range from between about 1.5 ft/min to about 108 ft/min. The linespeeds achieved by the process described herein allow the formation of commercially relevant quantities of CNS-laden substrates with short production times. For example, at 36 ft/min linespeed, the quantities of CNS-infused fibers (over 5% infused CNSs on fiber by weight) can exceed over 250 pound or more of material produced per day in a system that is designed to simultaneously process 5 separate rovings (50 lb/roving). Systems can be made to produce more rovings at once or at faster speeds by repeating growth zones. Moreover, some steps in the fabrication of CNSs, as known in the art, have prohibitively slow rates preventing a continuous mode of operation. For example, in a typical process known in the art, a CNS-forming catalyst reduction step can take 1-12 hours to perform. The process described herein overcomes such rate limiting steps.

The linespeeds achievable using processes of the invention are particular remarkable when considering that some steps in the fabrication of CNSs, as known in the art, have otherwise prohibitively slow rates, thus preventing a continuous mode of operation. For example, in a typical process known in the art, a CNS-forming catalyst reduction step can take 1-12 hours to perform. CNS growth itself can also be time consuming, for example requiring tens of minutes for CNS growth, precluding the rapid linespeeds realized in the present invention. The process described herein overcomes such rate limiting steps.

The CNS-laden substrate-forming processes of the invention can avoid CNS entanglement that occurs when trying to apply suspensions of pre-formed carbon nanotubes to substrates. That is, because pre-formed CNSs are not fused to the substrate, the CNSs tend to bundle and entangle. The result is a poorly uniform distribution of CNSs that weakly adhere to the substrate. However, processes of the present invention can provide, if desired, a highly uniform entangled CNS mat on the surface of the substrate by reducing the growth density. The CNSs grown at low density are infused in the substrate first. In such embodiments, the fibers do not grow dense enough to induce vertical alignment, the result is entangled mats on the substrate surfaces. By contrast, manual application of pre-formed CNSs does not insure uniform distribution and density of a CNS mat on the substrate.

Producing CNS-laden substrate 205 may include at least the operations of functionalizing a substrate to be receptive to barrier coating; applying a barrier coating and a CNS-forming catalyst to the substrate; heating the substrate to a temperature that is sufficient for carbon nanotube synthesis; and Synthesizing CNSs by CVD-mediated growth on the catalyst-laden fiber.

To prepare a substrate for barrier coating, functionalizing the substrate is performed. In some embodiments, functionalizing the substrate can include a wet chemical oxidative etch to create reactive functional groups (metal oxo and/or hydroxyl groups) on the substrate surface. This can be particularly useful when using zero-valent metals to create a surface oxide layer. In other embodiments, functionalizing can include a plasma process, which may serve a dual role of creating functional groups as described above, and roughening the substrate surface to enhance the surface area and wetting properties of the substrate, including the deposition of the barrier coating. To infuse carbon nanotubes into a substrate, the carbon nanotubes are synthesized on a substrate which is conformally coated with a barrier coating. In one embodiment, this is accomplished by conformally coating the substrate with a barrier coating and then disposing CNS-forming catalyst on the barrier coating. In some embodiments, the barrier coating can be partially cured prior to catalyst deposition. This can provide a surface that is receptive to receiving the catalyst and allowing it to embed in the barrier coating, including allowing surface contact between the CNS forming catalyst and the substrate. In such embodiments, the barrier coating can be fully cured after embedding the catalyst. In some embodiments, the barrier coating is conformally coated over the substrate simultaneously with deposition of the CNS-form catalyst. Once the CNS-forming catalyst and barrier coating are in place, the barrier coating can be fully cured.

In some embodiments, the barrier coating can be fully cured prior to catalyst deposition. In such embodiments, a fully cured barrier-coated substrate can be treated with a plasma to prepare the surface to accept the catalyst. For example, a plasma treated substrate having a cured barrier coating can provide a roughened surface in which the CNS-forming catalyst can be deposited. The plasma process for "roughing" the surface of the barrier coating thus facilitates catalyst deposition. The roughness is typically on the scale of nanometers. In the plasma treatment process craters or depressions are formed that are nanometers deep and nanometers in diameter. Such surface modification can be achieved using a plasma of any one or more of a variety of different gases, including, without limitation, argon, helium, oxygen, nitrogen, and hydrogen. In order to treat substrate in a continuous manner, 'atmospheric' plasma which does not require vacuum must be utilized. Plasma is created by applying voltage across two electrodes, which in turn ionizes the gaseous species between the two electrodes. A plasma environment can be applied to a fiber substrate in a 'downstream' manner in which the ionized gases are flowed down toward the substrate. It is also possible to send the fiber substrate between the two electrodes and into the plasma environment to be treated.

In some embodiments, the precursor substrate 305 can be treated with a plasma environment prior to barrier coating application. For example, a plasma treated substrate can have a higher surface energy and therefore allow for better wet-out and coverage of the barrier coating. The plasma process can also add roughness to the fiber surface allowing for better mechanical bonding of the barrier coating in the same manner as mentioned above.

The CNS catalyst can be prepared as a liquid solution that contains CNS-forming catalyst that includes transition metal nanoparticles. The diameters of the synthesized nanotubes are related to the size of the metal particles as described above. In some embodiments, commercial dispersions of CNS-forming transition metal nanoparticle catalyst are available and are used without dilution, in other embodiments commercial dispersions of catalyst can be diluted. Whether or not to dilute such solutions can depend on the desired density and length of CNS to be grown as described above.

In some embodiments, systems disclosed herein providing CNS growth chamber 320 may be further equipped with a feedback module, the feedback module configured to receive an output from the resistance measurement module, the feedback module being optionally in electronic communication with the CNS growth module and being capable of signaling a change in at least one growth condition in the CNS growth module. Thus, as the resistance of CNS-laden substrate 205 is being monitored, any change in observed resistance can be a signal of altered CNS loading on the substrate as the two are correlated as described above and shown in FIG. 1.

In some such embodiments, the at least one growth condition is selected from temperature, a partial pressure of a carbon feedstock gas, a partial pressure of an inert gas, linespeed, and combinations thereof. That is, if the resistance measurement indicates a deficiency in CNS coverage, operating conditions can be altered to compensate. This may be especially beneficial in longer synthesis runs where the buildup of carbonaceous materials on various parts of the synthesis apparatus may impact CNS growth efficiency. In some embodiments, the resistance data, and hence the CNS loading may indicate a halt to operations. In some embodiments, the resistance data may indicate simply adjusting any combination of the aforementioned parameters.

In some embodiments, the feedback module is configured to provide information to an operator in the form of a data log. In some such embodiments, the data log may simply indicate pass/fail criteria for quality control. Pass/fail criteria may include a measurement of CNS loading on the CNS-laden substrate. In some embodiments, where the feedback module reports directly to an operator via, for example, a monitor interface, the operating can make the decision on any parameter to alter. In some embodiments, the feedback module may report via an electronic signal to the growth chamber and its controls. In some such embodiments, the signal may indicate a halt in operations. In other embodiments, the signal may indicate and increase or decrease in temperature, a partial pressure of a carbon feedstock gas, a partial pressure of an inert gas, linespeed, and combinations thereof.

The system of the invention shown in FIGS. 2b and 3 include resistance measurement module having two point conductive contact 250, however, in some embodiments systems of the present invention may comprise a four point conductive contact, wherein an outer pair of contacts is configured to deliver a current, and an inner pair is configured to measure a voltage. By Ohm's law V=IR, the resistance can be determined as R=V/I. In some embodiments the four point contact may comprise conductive rollers allowing the advancement the CNS-laden substrate to a take-up spool 220 or similar collection mandrel.

Referring now to FIGS. 4a-g there are shown numerous configurations for threading substrate 205 through a four point conductive contact array, with pairs a/b, c/d, and e/f being degenerate. In some embodiments, the exact choice of configuration may depend on, inter alia, the desired tension on the substrate, the surface area of contact with the conductive roller, the flexibility of the substrate, and the like. In this regard, further adjustments may be made by disposition of the conductive contacts 250. Referring to FIGS. 5a-c, in some embodiments, the four point conductive contacts are co-linear, for example as indicated in FIG. 5a. In other embodiments, the four point conductive contacts are staggered as shown in FIGS. 5b and 5c. Note that lateral disposition of the conductive contacts can be especially effective in modulating the tension on the substrate. In some embodiments, the distance between a first and second contact and a third and forth contact are larger, individually, than the distance between the second contact and the third contact.

Systems of the invention may include even further contacts beyond a four point contact. In some such embodiments, one or more further contacts may be disposed between the outer pair, the additional contacts being further configured to take multiple voltage measurements. Such redundant voltage measurements may enhance the accuracy of the resistance measurements and may also, therefore, impact the accuracy of assessing CNS loading on the CNS-laden substrate. In some embodiments, the plurality of measured voltages may be averaged to arrive at an average resistance. In some embodiments, measurement of CNS loading on a CNS-laden substrate may provide the CNS loading figure with an accuracy in a range from about 0.01 weight percent to about 1.0 weight percent, including any value in between. In some embodiments, the accuracy can be in a range from about 0.01 weight percent to about 0.1 weight percent, including any value in between. In some embodiments, the accuracy can be in a range from about 0.1 weight percent to about 0.5 weight percent, including any value in between. The exact degree of accuracy may depend on, inter alia, the degree of CNS loading. For example, with detection at the linear portion of a calibration curve an accuracy of about one percent may read as an equivalent 48 ohm change in resistance. Assuming, for example, an ability to measure plus or minus about one ohm, a low end of detection, accounting for observed noise, may be as low as about 0.01 weight percent.

In accordance with the system embodiments disclosed herein above, the present invention further provides a method comprising continuously synthesizing carbon nanostructures (CNSs) on a substrate in a CNS growth chamber to provide a CNS-laden substrate and continuously monitoring the resistance of the CNS-laden substrate exiting a distal end of the growth chamber, as exemplified in FIG. 3. Methods of the invention may include continuously monitoring the resistance of the CNS-laden substrate, such monitoring comprising applying an electric field to the CNS-laden substrate or applying a current to the substrate and measuring at least one voltage.

In some embodiments, methods of the invention may further comprise altering growth conditions in the CNS growth chamber in response to a threshold resistance measurement. In some such embodiments, this may include altering synthesis parameters, halting synthesis, any of which may be accomplished by an operator or, by a signal from the resistance measurement module to the CNS growth chamber.

To facilitate a better understanding of the present invention, the following examples of preferred embodiments are given. In no way should the following examples be read to limit, or to define, the scope of the invention.

EXAMPLE

This example demonstrates the detection capability of an in-line resistance monitoring system coupled with a continuous CNS-infused glass fiber growth system. In this case, detection of CNS as a function of weight percentage of the final fiber form is shown between 6-11% weight CNS on glass fiber.

FIG. 3 depicts system 300 for producing CNS-infused fiber and continuously monitoring fiber resistance. System 300 includes a CNS growth chamber 310 which receives a catalyst laden precursor substrate 305. CNS synthesis occurs in chamber 310, to provide CNS-laden substrate 205 at its distal end. Substrate 205 is delivered to resistance measurement module 210 and wound on take-up spool 230.

Catalyst laden precursor substrate 305 consists of a E-glass fiber which has been catalyzed in a previous process with an iron-based catalyst. In this example, the input catalyst laden precurson substrate 305 remains constant.

The catalyst laden precursor substrate 305 is drawn through CNS growth chamber 310 at a constant rate of 6.1 meters per minute by take up spool 230. The CNS growth system is maintained at a constant growth temperature of 700-800° C. Nitrogen gas is utilized as the inert carrier gas and a hydrocarbon gas such as ethylene, ethane, acetylene, or methane is used as the reactant gas. The ratio of hydrocarbon gas to nitrogen gas is held constant at 0.3 and the total flow rate is modulated between 1.5-3 liters per minute.

By modulating the total flow of the incoming gas and maintaining a constant growth temperature and substrate feed rate, CNS-laden substrate 205 has a controlled amount of CNS growth described by weight percentage of total final fiber weight of between 6 and 11 percent.

CNS-laden substrate 205 is then drawn through a 2-point resistance measurement module 210 which utilizes conductive rollers and bearings to transfer a current supplied by ohm meter 260. Ohm meter 260 is coupled to a data acquisition system (not shown) which continuously acquires resistance measurement data for future correlation to measured CNS weight percent data.

After the CNS laden substrate 205 is drawn through resistance measurement module 210, it is finally wound at take-up spool 230.

Figure 6:
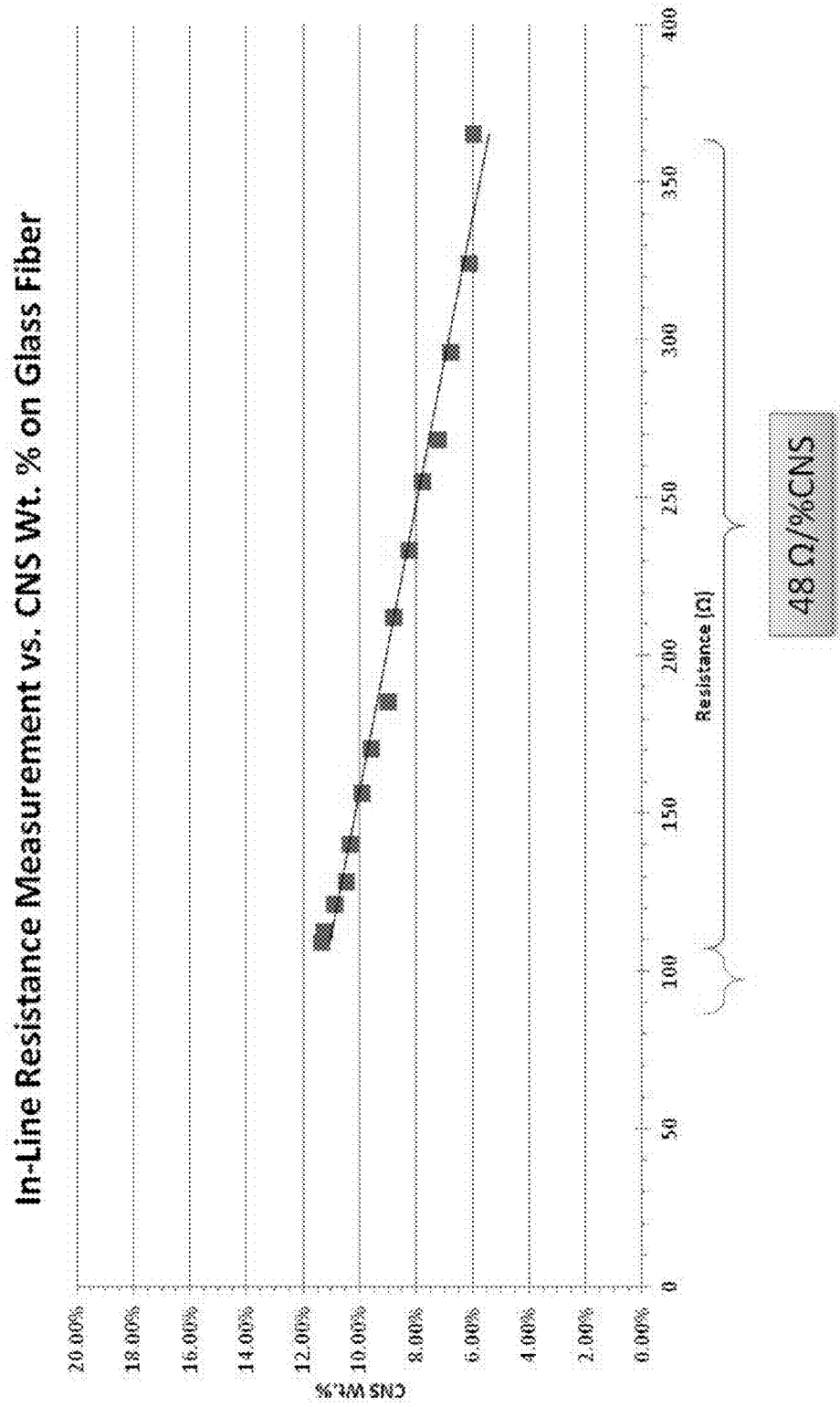
FIG. 6 shows a plot corresponding to carbon nanostructure loading with substrate resistance for CNS-infused fiberglass tow in a range in which about 5 percent to about 15 percent of the fiber weight consisted of CNS.

The data collected as a result of this example is shown in FIG. 6. The correlation curve demonstrates a linear relationship between CNS weight percentage on glass fiber between 6-11% where the increase is resistance is approximately 48 ohms per 1 weight percent CNS on fiber. Based on the noise measured during this example of about 1 ohm, a measurement resolution of approximately 0.02 weight percentage on CNS-infused fiber is expected.

It is to be understood that the above-described embodiments are merely illustrative of the present invention and that many variations of the above-described embodiments can be devised by those skilled in the art without departing from the scope of the invention. For example, in this Specification, numerous specific details are provided in order to provide a thorough description and understanding of the illustrative embodiments of the present invention. Those skilled in the art will recognize, however, that the invention can be practiced without one or more of those details, or with other processes, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

The invention claimed is:

1. A quality control system for the manufacture of carbon nanostructure-laden fibers or fabrics comprising a resistance measurement module configured to receive a carbon nanostructure (CNS)-laden fiber or fabric in motion for continuously measuring resistance of the CNS-laden fiber or fabric as the CNS-laden fiber or fabric moves across the resistance measurement module, wherein:
- the resistance measurement module comprises at least a two point conductive contact with the CNT-laden fiber or fabric,
- the two point conductive contact is configured to modulate tension on the CNS-laden fiber or fabric over the two point conductive contact as the CNS-laden fiber or fabric moves across the resistance measurement module, and
- the two point conductive contact is configured to be in contact with different positions of the CNS-laden fiber or fabric as the CNS-laden fiber or fabric moves across the resistance measurement module.

2. The system of claim 1, wherein the resistance measurement module is configured to measure resistance via an electric field or inductive based measurement.

3. The system of claim 1, wherein the CNS-laden fiber or fabric is configured to be fed continuously to the resistance measurement module from a CNS growth module, the CNS growth module configured to continuously synthesize CNSs on a substrate precursor.

4. The system of claim 3, further equipped with a feedback module, the feedback module configured to receive an output from the resistance measurement module; the feedback module being optionally in electronic communication with the CNS growth module and being capable of signaling a change in at least one growth condition in the CNS growth module.

5. The system of claim 4, wherein the at least one growth condition is selected from temperature, a partial pressure of a carbon feedstock gas, a partial pressure of an inert gas, linespeed, and combinations thereof.

6. The system of claim 4, wherein the feedback module is configured to provide information to an operator in the form of a data log.

7. The system of claim 6, wherein the data log indicates pass/fail criteria for quality control.

8. The system of claim 7, wherein pass/fail criteria comprises a measurement of CNS loading on the CNS-laden fiber or fabric.

9. The system of claim 1, the at least a two point conductive contact comprising four point conductive contacts, wherein an outer pair of contacts is configured to deliver a current, and an inner pair is configured to measure a voltage.

10. The system of claim 9, wherein the four point contact comprises conductive rollers allowing the advancement the CNS-laden fiber or fabric to a collection mandrel.

11. The system of claim 9, one or more further contacts disposed between the outer pair configured to take multiple voltage measurements.

12. The system of claim 9, wherein the four point conductive contacts are co-linear.

13. The system of claim 9, wherein the four point conductive contacts are staggered.

14. The system of claim 9, wherein the distance between a first and second contact and a third and fourth contact are larger, individually, than the distance between the second contact and the third contact.

15. A method comprising:
- continuously synthesizing carbon nanostructures (CNSs) on a fiber or fabric in a CNS growth chamber to provide a moving CNS-laden fiber or fabric;
- continuously receiving, over at least a two point conductive contact, the moving CNS-laden fiber or fabric exiting a distal end of the growth chamber, wherein the two point conductive contact modulates tension on the moving CNS-laden fiber or fabric over the two point conductive contact; and
- continuously monitoring resistance of the moving CNS-laden fiber or fabric; wherein the two point conductive contact is configured to be in contact with different positions of the CNS-laden fiber or fabric as the CNS-laden fiber or fabric is moving.

16. The method of claim 15, wherein continuously monitoring the resistance of the moving CNS-laden fiber or fabric comprises applying an electric field to the moving CNS-laden fiber or fabric.

17. The method of claim 15, wherein continuously monitoring the resistance of the moving CNS-laden fiber or fabric comprises applying a current to the moving CNS-laden fiber or fabric and measuring at least one voltage.

18. The method of claim 15, further comprising altering growth conditions in the CNS growth chamber in response to a threshold resistance measurement.

19. The system of claim 1, wherein the two point conductive contact is configured to move along the CNS-laden fiber or fabric.

20. The method of claim 15, wherein the continuously monitoring comprises continuously measuring the resistance of the moving CNS-laden fiber or fabric across a length between the two point conductive contact.

* * * * *